(12) United States Patent
Davis et al.

(10) Patent No.: US 6,600,037 B1
(45) Date of Patent: Jul. 29, 2003

(54) 4,5-DISUBSTITUTED-2-AMINOPYRIMIDINES

(75) Inventors: Jeremy Martin Davis, Wokingham (GB); David Festus Charles Moffat, Maidenhead (GB)

(73) Assignee: Celltech R & D Limited (GB)

( * ) Notice: Subject to any disclaimer, the term of this patent is extended or adjusted under 35 U.S.C. 154(b) by 0 days.

(21) Appl. No.: 09/692,368

(22) Filed: Oct. 19, 2000

(30) Foreign Application Priority Data

Oct. 20, 1999 (GB) .............................. 9924862

(51) Int. Cl.⁷ ..................... C07D 239/42; C07D 401/12
(52) U.S. Cl. .................... 544/60; 544/122; 544/330; 544/331; 544/332
(58) Field of Search ................. 514/227.8, 252.14, 514/252.18, 275; 544/60, 331, 332, 330, 122

(56) References Cited

U.S. PATENT DOCUMENTS

| | | | |
|---|---|---|---|
| 3,947,467 A | 3/1976 | Verge et al. | 260/310 R |
| 4,012,495 A | 3/1977 | Schmiechen et al. | 514/424 |
| 4,015,017 A | 3/1977 | Gazave et al. | 514/687 |
| 4,153,713 A | 5/1979 | Huth et al. | 514/423 |
| 4,193,926 A | 3/1980 | Schmiechen et al. | 548/517 |
| 4,303,649 A | 12/1981 | Jones | 514/8 |
| 4,548,940 A | 10/1985 | Ife | 514/272 |
| 4,659,363 A | 4/1987 | Hubele et al. | 71/92 |
| 4,694,009 A | 9/1987 | Hubele et al. | 514/269 |
| 4,788,195 A | 11/1988 | Torley et al. | 514/252 |
| 4,792,561 A | 12/1988 | Walker et al. | 514/312 |
| 4,876,252 A | 10/1989 | Torley et al. | 514/224.8 |
| 4,897,396 A | 1/1990 | Hubele | 514/275 |
| 4,921,862 A | 5/1990 | Walker et al. | 514/312 |
| 4,966,622 A | 10/1990 | Rempfler et al. | 71/92 |
| 4,971,959 A | 11/1990 | Hawkins | 514/150 |
| 4,973,690 A | 11/1990 | Rempfler et al. | 544/279 |
| 4,987,132 A | 1/1991 | Mase et al. | 514/252 |
| 5,124,455 A | 6/1992 | Lombardo | 546/181 |
| 5,128,358 A | 7/1992 | Saccomano et al. | 514/392 |
| 5,159,078 A | 10/1992 | Rempfler et al. | 544/330 |
| 5,164,372 A | 11/1992 | Matsuo et al. | 514/19 |
| 5,175,167 A | 12/1992 | Zipperer et al. | 514/277 |
| 5,177,085 A | 1/1993 | Naef | 514/307 |
| 5,236,918 A | 8/1993 | Amschler et al. | 514/247 |
| 5,274,002 A | 12/1993 | Hawkins | 514/530 |
| 5,298,511 A | 3/1994 | Waterson | 514/311 |
| 5,326,898 A | 7/1994 | Chandraratna | 560/17 |
| 5,340,827 A | 8/1994 | Beeley et al. | 514/352 |
| 5,491,147 A | 2/1996 | Boyd et al. | 514/247 |
| 5,521,184 A | 5/1996 | Zimmermann | 514/252 |
| 5,550,137 A | 8/1996 | Beeley et al. | 514/354 |
| 5,580,888 A | 12/1996 | Warrellow et al. | 514/332 |
| 5,593,997 A | 1/1997 | Dow et al. | 514/258 |
| 5,608,070 A | 3/1997 | Alexander et al. | 546/270 |
| 5,622,977 A | 4/1997 | Warrellow et al. | 514/336 |
| 5,633,257 A | 5/1997 | Warrellow et al. | 514/277 |
| 5,674,880 A | 10/1997 | Boyd et al. | 514/307 |
| 5,691,376 A | 11/1997 | Caggiano et al. | 514/532 |

(List continued on next page.)

FOREIGN PATENT DOCUMENTS

| | | |
|---|---|---|
| DE | 250 1443 | 7/1975 |
| DE | 34 36 380 A1 | 4/1986 |
| EP | 0 233 461 A2 | 8/1987 |
| EP | 0 295 210 A1 | 12/1988 |
| EP | 0 337 943 A2 | 10/1989 |
| EP | 0 393 500 A1 | 10/1990 |
| EP | 0 490 823 A1 | 6/1991 |
| EP | 0 470 805 A1 | 2/1992 |
| EP | 0 497 564 A1 | 8/1992 |
| EP | 0 511 865 A1 | 11/1992 |

(List continued on next page.)

OTHER PUBLICATIONS

Ames, D.E. et al., "Some Dipyridylalkanes", *J. Chem. Soc.*, 1962, 1475–1481.

(List continued on next page.)

*Primary Examiner*—Deepak Rao
(74) *Attorney, Agent, or Firm*—Woodcock Washburn LLP

(57) ABSTRACT

Pyrimidines of formla (1) are described:

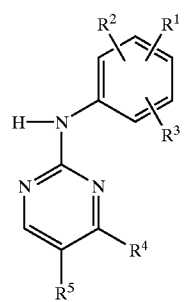

(1)

wherein
$R^1$ is a —$XR^6$ group;
$R^2$ and $R^3$ which may be the same or different is each a hydrogen or halogen atom or a group selected from an optionally substituted aliphatic, cycloaliphatic, heteroaliphatic, heterocycloaliphatic, —OH, —$OR^{10}$ [where $R^{10}$ is an optionally substituted aliphatic, cycloaliphatic, heteroaliphatic, heterocycloaliphatic, aromatic or heteroaromatic group] —SH, —$NO_2$, —CN, —$SR^{10}$, —$COR^{10}$, $S(O)R^{10}$, —$SO_2R^8$, —$SO_2N(R^8)(R^9)$, —$CO_2R^8$, —$CON(R^8)(R^9)$, —$CSN(R^8)(R^9)$, —$NH_2$ or substituted amino group;
$R^4$ is a $X^1R^{11}$ group where $X^1$ is a covalent bond or a —$C(R^{12})(R^{13})$— [where each of $R^{12}$ and $R^{13}$ is a hydrogen or halogen atom or a hydroxyl, alkyl or haloalkyl group] or —C(O)— group and $R^{11}$ is an optionally substituted phenyl, thienyl, thiazolyl or indolyl group;
$R^5$ is a halogen atom or an alkynyl group;
and the salts, solvates, hydrates and N-oxides thereof.

The compounds are selective KDR kinase and/or FGFr kinase inhibitors and are of use in the prophylaxis and treatment of disease states associated with angiogenesis.

2 Claims, No Drawings

U.S. PATENT DOCUMENTS

| | | | |
|---|---|---|---|
| 5,693,659 A | 12/1997 | Head et al. | 514/357 |
| 5,698,711 A | 12/1997 | Palfreyman | 549/66 |
| 5,716,967 A | 2/1998 | Kleinman | 514/313 |
| 5,723,460 A | 3/1998 | Warrellow et al. | 514/247 |
| 5,728,708 A | 3/1998 | Zimmermann | 514/275 |
| 5,739,144 A | 4/1998 | Warrellow et al. | 514/277 |
| 5,753,663 A | 5/1998 | Flippin et al. | 514/257 |
| 5,776,958 A | 7/1998 | Warrellow et al. | 514/345 |
| 5,780,477 A | 7/1998 | Head et al. | 514/277 |
| 5,780,478 A | 7/1998 | Alexander et al. | 514/277 |
| 5,786,354 A | 7/1998 | Warrellow et al. | 514/277 |
| 5,798,373 A | 8/1998 | Warrellow | 514/357 |
| 5,849,770 A | 12/1998 | Head et al. | 514/357 |
| 5,851,784 A | 12/1998 | Owens et al. | 435/19 |
| 5,859,034 A | 1/1999 | Warrellow et al. | 514/357 |
| 5,866,593 A | 2/1999 | Warrellow et al. | 514/336 |
| 5,891,896 A | 4/1999 | Warrellow et al. | 514/357 |
| 5,922,741 A | 7/1999 | Davis et al. | 514/341 |
| 5,958,935 A * | 9/1999 | Davis et al. | 514/275 |
| 6,057,329 A | 5/2000 | Davis et al. | 514/267 |
| 6,080,790 A | 6/2000 | Boyd et al. | 514/650 |
| 6,093,716 A | 7/2000 | Davis et al. | 514/253 |
| 6,096,747 A | 8/2000 | Beeley et al. | 514/256 |
| 6,235,746 B1 * | 5/2001 | Davis et al. | 514/275 |

FOREIGN PATENT DOCUMENTS

| | | |
|---|---|---|
| EP | 0 537 742 A2 | 4/1993 |
| EP | 0 564 409 A1 | 10/1993 |
| FR | 1 285 932 | 8/1972 |
| FR | 2 545 356 A1 | 11/1984 |
| GB | 2 313 422 | 12/1976 |
| GB | 1588639 | 4/1981 |
| JP | 61-112059 | 5/1986 |
| JP | 3-77872 | 4/1991 |
| JP | 3-77923 | 4/1991 |
| WO | WO 86/02353 | 4/1986 |
| WO | WO 87/06576 | 11/1987 |
| WO | WO 91/15451 | 10/1991 |
| WO | WO 91/16892 | 11/1991 |
| WO | WO 92/00968 | 1/1992 |
| WO | WO 92/06085 | 4/1992 |
| WO | WO 92/06963 | 4/1992 |
| WO | WO 92/07567 | 5/1992 |
| WO | WO 92/12961 | 8/1992 |
| WO | WO 92/19594 | 11/1992 |
| WO | WO 92/19602 | 11/1992 |
| WO | WO 93/10118 | 5/1993 |
| WO | WO 93/19748 | 10/1993 |
| WO | WO 94/02465 | 2/1994 |
| WO | WO 94/10118 | 5/1994 |
| WO | WO 94/12461 | 6/1994 |
| WO | WO 94/13661 | 6/1994 |
| WO | WO 94/14742 | 7/1994 |
| WO | WO 94/20446 | 9/1994 |
| WO | WO 94/20455 | 9/1994 |
| WO | WO 95/04046 | 2/1995 |
| WO | WO 95/09847 | 4/1995 |
| WO | WO 95/09851 | 4/1995 |
| WO | WO 95/09852 | 4/1995 |
| WO | WO 95/09853 | 4/1995 |
| WO | WO 95/17386 | 6/1995 |
| WO | WO 95/31451 | 11/1995 |
| WO | WO 95/33727 | 12/1995 |
| WO | WO 95/35281 | 12/1995 |
| WO | WO 95/35283 | 12/1995 |
| WO | WO 96/14843 | 5/1996 |
| WO | WO 97/09297 | 3/1997 |
| WO | WO 97/09325 | 3/1997 |
| WO | WO 98/28281 | 7/1998 |
| WO | WO 98/58926 | 12/1998 |
| WO | WO 99/31073 | 6/1999 |
| WO | WO 00/27825 | 5/2000 |

OTHER PUBLICATIONS

Ashton, M.J., et al., "Selective Type IV Phosphodiesterase Inhibitors as Antiasthmatic Agents. The Syntheses and Biological Activities of 3–(Cyclopentyloxy)–4–methoxybenzamides and Analogues", *J. Med. Chem.*, 1994, 37, 1696–1703.

Barton, D. et al., "A useful synthesis of pyrroles from nitroolefins", *Tetrahedron*, 1990, 46(21), 7587–7587 (HCAPLUS) 1991:163917, 3 pages).

Beavo & Reifsynder, "Primary Sequence of Cyclic Nucleotide Phosphodiesterase Isozymes and the Design of Selective Inhibitors" *TIPS*, 1990, 11, 150–155.

Buu–Hoi, N.P. et al., "Bromination of Some 1,2,2–Triarylethylenes" *J. Organic Chemistry*, 1958, 23, 1261–1263.

Buu–Hoi et al., "New Method for the Synthesis of ω,ω–Diarylacetophenones Aminated in the Aromatic Nucleus. Polynitration of Triarylethylenes", 1964, 61(13), 1600h, *Reported on CAS, Chem. Abstr. Bull. Soc. Chim. France*, 1964, 8, 1842–1844.

Bortolus et al., "cis–trans Isomerization of azastilbenes photosensitized by biacetyl", *Mol. Photochem.*, 1970, 2(4), 311–321, CAPLUS accession No. 1971–434722, 2 pages.

Chan, A.C. et al., "The Role of Protein Tyrosine Kinases and Protein Tyrosine Phosphatases in T Cell Antigen Receptor Signal Transduction", *Annu. Rev. Immunol.*, 1994, 12, 555–592.

Chatterjee, A. et al., "Total Synthesis of Ring–C Aromatic 18–Nor Steroid", *Tetrahedron*, 1980, 36, 2513–2519.

Chemical Abstracts, "Hypoglycemic Pharmaceuticals Containing Manzammide Derivatives", *Chem. Abstr.*, 1983, 99(6), No. 43558Z, Reported as JP Patent.

Chemical Abstracts. Registry Handbook—Number Section. Printed Issues Columbus US *compounds with registry numbers 95992–21–5 (CARHBT(RN1) 1RN–1648RN(1985); 95971–60–1 (CARHBT(RN1) 1RN–1648RN(1985); 90053–37–5 (CARHBT(RM1) 1RM–1426RM(1984); 82668–18–6 (CARHBT(RK2) 1515RK–2955RK(1982); 80395–25–1 (CARHBT(RK1)1RK–1514RK(1982); 49610–49–3 (CARHBT(RC1)1RC–1650RC(1974).

Chemical Abstracts, Registry No. 2732–15–2, prior to 1967, 1 page.

Chemical Abstracts, Registry No. 4593–13–9, prior to 1967, 1 page.

Clayton, S.E. et al., "Direct Aromatic tert–Butylation during the Synthesis of Thiochroman–4–ones", *Tetrahedron*, 1993, 49(4), 939–946.

Collins, R.F. et al., "The Chemotherapy of Schistosomiasis. Part IV. Some Ethers of 4–Amino–2–methoxyphenol", *J. Chem. Soc.*, 1961, 1863–1879.

Daves, G.D. et al., "Pyrimidines. XIII. 2– and 6–Substituted 4–Pyrimidinecarboxylic Acids", *J. Het. Chem.*, 1964, 1, 130–133.

Degani, I. et al., "Cationi etero–aromatici Nota VI—Sintesi di alcuni derivati del perclorato di tiacromilio", *Boll. Sci. Fac. Chem. Ind. Bologna*, 1966, 24(2–3), 75–91 (English Summary Only).

Dietl, F. et al., "Chinone von Benzo–und Dibenzokronethern", *Synthesis*, 1985, 626–631 (English summary only).

Dent, G., et al., "Inhibition of eosinophil cyclic nucleotide PDE activity and opsonised zymosan–stimulated respiratory burst by 'type IV'–selective PDE inhibitors", *Br. J. Pharmacol.*, 1991, 103, 1339–1346.

El–Wakil et al., "Study of the proton magnetic resonance of methoxytamoxifen towards ortho–substitution", *Chem. Abstr.*, 1992, 116, 255248t, Reported in CAS, Soectrisc, Kett,M 1992, 25(3), 401–407.

Fitzgerald, J.J. et al., "Reaction of benzocyclobutene oxides with nitriles: synthesis of hypecumine and other 3–substituted isoquinolines", *Tetrahedron Lett.*, 1994, 35(49), 9191–9194 (HCAPLUS 1995:272292, 2 pages).

Geissler, J.F. et al., "Thiazolidine–Diones. Biochemical and Biological Activity of a Novel Class of Tyrosine Protein Kinase Inhibitors", *J. Biol. Chem.*, 1990, 265(36), 22255–22261.

Grammaticakis, P., "Contribution A L'Etude de L'Absortion Dans L'Ultraviolet Moyen Et Le Visible Des N–Aroyl–Arylamines. IV. 2,3–, 3,4– et 2,4–, dimethoxybenzoylarylamines", *Bulletin dela Societa Chemique de France*, 1965 848–858.

Green and Wuts, "Protective Group in Organic Synthesis", John Wiley & Sons, New York, 1991.

Griffin, R.W. et al., "1–Methyl–7–halo–2–naphthalenecarboxylic Acid Derivatives", *J. Organic Chem.*, 1964, 29(8), 2109–2116.

Gupta, A.S. et al., "Friedel–Crafts Condensation of Ethyl Allylmalonate with Anisole", *Tetrahedron*, 1967, 23, 2481–2490.

Hanks, S.K. et al., "The eukaryotic protein kinase superfamily: kinase (catalytic) domain structure and classification", *FASEB J.*, 1995, 9, 576–596.

Hanna, M.M. et al., "Synthesis and antimicrobial activity of some substituted 3–aryl–5–benzylidene–2–phenyl–4–imidazolone derivatives", *Bull. Fac. Pharm.*, 1994, 32(3), 353–359 (HCAPLUS 1996:586501, 2 pages).

Hart, H., et al., "Alkylation of Phenol with a Homoallylic Halide", *J. Am. Chem. Soc.*, 1963, 85, 3269–3273.

Heaslip, R.J., et al., "Phosphodiesterase–IV Inhibition, Respiratory Muscle Relaxation and Bronchodilation by WAY–PDA–641", *J. Pharm. Exper. Ther.*, 1994, 268(2), 888–896.

Hirose, H., et al., "Styrene Derivatives and Electrophotoraphic Photoreceptor Containing Them", *Chem. Abstr.*, 1993, 118, 136183z, Japanese Patent.

Ife, R.J., "Aminopyrimidinone derivaties as histamine H1–antagonists", CAPLUS Abstract No. 101:211163, Registry No. 92993–05–0, Jul. 4, 1984, 2 pages, EPO Patent.

Ishikura, M. et al., "An Efficient Synthesis of 3–Heteroarylpyridines via Diethyl–(3–pyridyl)–borane" *Synthesis*, 1984, 936–938.

Iwashita, S. et al., "Signal Transduction System for Growth Factor Receptors Associated with Tyrosine Kinase Activity: Epidermal Growth Factor Receptor Signaling and Its Regulation", *Cellular Signalling*, 1992, 4(2), 123–132.

Johnson, A.T., et al., "Identification of Retinoic Acid Receptor β Subtype Specific Agonists", *J. Med. Chem.*, 1996, 39(26), 5027–5030.

Kaiser, E.M., et al., "Selective metalations of methylated pyridines and quinolines", *J. Org. Chem.*, 1973, 38(1), 71–75, CAPLUS accession No. 1973–71853, 2 pages.

Karlsson, J.A., et al., "Anti–inflammatory effects of novel selective cyclic nucleotide phosphodiesterase inhibitors," in "T–Lymphocyte and Inflammatory Cell Research in Asthma", Joller, G. et al. (eds.), Academic Press, 1993, 323–347.

Kefalas, P. et al., "Signalling by the p60$^{c-src}$ Family of Protein–Tyrosine Kinases", *Int. J. Biochem. Cell Biol.*, 1995, 27(6), 551–563.

Kroon, A.P., et al., "On the occurrence of an $S_n$(ANRORC) mechanism in the amination of 2–substituted 4–phenylpyrimidines with potassium amide in liquid ammonia," *J. Royal Netherlands Chem. Soc.*, 1974, 93(12), 325–328.

Lehmann, J. et al., "Lactones; XIII. Grignard Reaction Followed by Phase–Transfer Oxidation: A Convenient Synthesis of γ,γ–Distributed γ–Butyrolactones from γ–Butyrolactone", *Synthesis*, 1987, 1064–1067 (English abstract only).

Lisle, H. et al., "IL–5–Induced Eosinophilia in the Rat Pleural Cavity: The Effect of Dexamethasone and Indomethacin", *Br. J. Pharmacol.* 1993, 108, 230.

Livi, G.P., et al., "Cloning and Expression of cDNA for a Human Low-$K_m$, Rolipram–sensitive Cyclic AMP Phosphodiesterase", *Molecular and Cellular Biol.* 1990, 10(6), 2678–2686.

Manhas, M.S., et al., "heterocyclic Compounds XII. Quinazoline Derivatives as Potential Antifertility Agents(1)" *J. Heterocyclic Chem.*, 1979, 16, 711–715.

Mathison, I.W., et al., "Synthesis and Hypotensive Properties of Tetrahydroisoquinolines", *J. Med. Chem.*, 1973, 16(4), 332–336.

Meyers, A.I. et al., "Oxazolines. XI. Synthesis of Functionalized Aromatic and Aliphatic Acids. A Useful Protecting Group for Carboxylic Acids Against Grignard and Hydride Reagents", *J. Org. Chem.* 1974, 39(18), 2787–2793.

Meyers, A.I. et al., "The Synthesis of 2–Pyridones from Cyclic Cyano Ketones. A New Aromatization Procedure for Dihydro–2–pyridones", *J. Org. Chem.*, 1964, 29, 1435–1438.

Mezheritskaya, L.V., et al., "Synthesis and properties of carboxonium het=erocyclic systems. VII. Synthesis and properties of 2–benzyl–substituted 1,3–dioxolanium salts", *Chem. Abstr.*, 1980, 93, 95160j, 635, Zh. Org. Khim, 1980, 16(1), 183–188.

Mitsunobu, O., "The Use of Diethyl Azodicarboxylate and Triphenylphosphine in Synthesis and Transformation of Natural Products" *Synthesis*, 1981, 1–28.

Miyaura, N. et al., "The Palladium–Catalyzed Cross–Coupling Reaction of Phenylboronic Acid with Haloarenes in the Presence of Bases", *Synth. Comm.*, 1981, 11(7), 513–519.

Nanjo, K., et al., "Preparation of 2–anilinopyrimidines as agricultural fungicides", *Chem. Abstr.*, 1992, 116(21), No. 116:209603q, JP Patent.

Newton, A.C., "Protein Kinase C: Structure, Function, Regulation", *J. Biol. Chem.*, 1995, 270(48), 28495–28498.

Nicholson, C.D., et al., "Differential Modulation of Tissue Function and Therapeutic Potential of Selective Inhibitors of Cyclic Nucleotide Phosphodiesterase Isoenzymes" *TIPS*, 1991, 12, 19–27.

O'Connor, J.J., et al., "Voltammetry and Controlled Potential Oxidation of 3,4–dimethoxypropenylbenzene at a rotating platinum electrode in unbuffered acetonitrile and in acetonitrile–pyridine solution" Reported in Chem. Abstr., 1964, 60(8) #10203.4, J. Electrochem. Soc., 1964, 111(3), 335–343.

Ohtani, Y. et al., "Studies on Pitch Problems Caused by Pulping and Bleaching of Tropical Woods. XIV. Chemistry of the Aurone Derivatives at the Conventional Bleaching Stages", Acta Chem. Scand., 1982, 613–621.

Pickett, W.C. et al., "Modulation of Eicosanoid Biosynthesis by Novel Pyridinylpyrimidines", Ann. N.Y. Acad. Sci., 1994, 744, 299–305.

Pines, J., "Cyclins and cyclin–dependent kinases: take your partners", TIBS, 1993, 18, 195–197.

Plé, N. et al., "Metalation of Diazines. XI. Directed Ortho–Lithiation of Fluoropyrimidines and Applicaiton to Synthesis of an Azacarboline", J. Heterocylic Chem., 1994, 31, 1311–1315.

Porter, R.A., et al., "Preparation of 6–phenyl–3–(5–tetrazolyl)pyridin–2(H)–one Derivatives as Cyclic AMP–dependent Protein Kinase Agonists" Chem. Abstr., 1992, 117(9), 90296n, PCT Application.

Ramalingam, T., et al., "Synthesis and Pharmacology of 2,5–Disubstituted 1,3,4–Oxadiazoles" J. Indian Chem. Soc., 1981, 58(3), 269–271.

Reddy, K.B., et al., "Inhibition of Breast Cancer Cell Growth in Vitro by a Tyrosine Kinase Inhibitor" Cancer Research, 1992, 52, 3636–3641.

Sakakibara, K. et al., "Preparation of N–pyridyl–4–(benzyloxy)benzamides as Cardiotonics", Chem. Abstr., 1988, 108, No. 131583p, JP Patent.

Sánchez, I.H., et al., "Formal Total Synthesis of β–Pipitzol", Tetrahedron, 1985, 41(12), 2355–2359.

Schneider, M.R., et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inihibiting Activites", J. Med. Chem., 1986, 29, 1355–1362.

Seitz, D.E., et al., "Fluorotamoxifen. A Caveat on the Generality of Electrophilic Destannylation" Reported in Chem. Abstr., 1989, 111, 57133k, Synth. Comm., 1988, 18(18), 2353–2357.

Sharp, M.J. et al., "Synthetic Connections to the Aromatic directed Metalation Reaction. Functionalized Aryl Boronic Acids by Ipso Borodesilylation; General Synthesis of Unsymmetrical iphenyls and m–Terphenyls", Tetrahderon Lett., 1987, 28(43), 5093–5096.

Shiori, T., et al., "New Methods and Reagents in Organic Synthesis. 3. Diethyl Phosphoroacyanidate: A New Reagent for C–Acylation", J. Org. Chem., 1978, 43(18), 3631–3632.

Spada, A.P. et al., "Small Molecule Inhibitors of Tyrosine Kinase Activity", Exp. Opin. Ther. Patents, 1995, 5(8), 805–817.

Takeuchi, I. et al., "On the Antimocrobial Activity and Syntheses of Carbanilide and Salicylanilide Derivatives", Reported in Chem. Abstr., 1983, 98, No. 125577y, Yakugaku Zasshi, 1982, 102(11), 1028–1030.

Thompson, W.J. and Guadino, J., "A General Synthesis of 5–Arylnicotinates" J. Org. Chem., 1984, 49, 5237–5243.

Tollari, S. et al., "Intramolecular amination of olefins. Synthesis of 2–substituted–4–quinolones from 2–nitrochalcones catalyzed by ruthenium", J. Chem. Soc. Chem. Commun., 1994, 15, 1741–1742 (HCAPLUS 1994:605194, 2 pages).

Tominaga, Y., et al., "Polarized Ethylenes. IV. Synthesis of Polarized Ethylenes Using Thioamides and Methyl Dithiocarboxylates and Their Application to Syntheses of Pyrazoles, Pyrimidines, Pyrazolo[3,4–d]pyrimidines, and 5–Aza [2.2.3]cyclazines", J. Het. Chem., 1990, 27, 647–660.

Trost and Fleming (eds.), Comprehensive Organic Synthesis, Pergamon Press, New York, 1991, 3, 531–541.

Tsutsumi, K. et al., "Preparation of (Dialkoxyphosphinoylmethyl) benzamides as Antihyperlipidemics", Chem. Abstr., 1990, 113, No. 6599a, UK Patent.

Vidal, J., et al., "Electrophilic Amination: Preparation and Use of N–Boc–3–(4–cyanophenyl)oxaziridine, a New Reagent That Transfers a N–Boc Group to N– and C–Nucleophiles", J. Org. Chem., 1993, 58, 4791–4793.

Yamaguchi, H., "Guanidinobenzene derivatives as anticoagulants", Chem. Absts., 1989, 110, 655 (Abstract No. 94706z), JP Patent.

Yamato, M. et al., "Chemical structure and sweet taste of isocoumarin and related compounds. VI", Chem. Pharm. Bull., 1975, 23(12), 3101–3105 (HCAPLUS 1976:99154, 2 pages).

Yeadon, M., et al., "Mechanisms Contributing to Ozone–Induced Bronchial Hyperreactivity in Guinea Pigs", Pulmonary Pharm., 1992, 5, 39–50.

Yoneda, T., et al., "The Antiproliferative Effects of Tyrosine Kinase Inhibitors Tyrphostins on a Human Squamous Cell Carcinoma in Vitro and in Nude Mice" Cancer Research, 1991, 51, 4430–4435.

Zimmermann, J., et al., "Phenylamino–Pyrimidine (PAP) Deirvatives: A New Class of Potent and Selective Inhibitors of Protein Kinase C(PKC)", Arch. Pharm. Pharm. Med. Chem., 1996, 329(7), 371–376.

Zimmermann, J., et al., "Phenylamino–Pyrimidine (PAP)–Derivatives: A New Class of Potent and Highly Selective PDGF–Receptor Autophosphorlation Inhibitors," Bioorg. Med. Chem. Lett., 1996, 6(11), 1221–1226.

Zimmermann, J., et al., "Potent and Selective Inhibitors of the ABL–Kinase Phenylamino–Pyrimidine (PAP) Derivatives," Bioorg. Med. Chem. Lett., 1997, 7(2), 187–192.

Borgstrom, P., et al., "Complete inhibition of angiogenesis and growth of microtumors by anti–vascular endothelial growth factor neutralizing antibody: novel concepts of angiostatic therapy from intravital videomicroscopy," Cancer Res., 1996, 56, 4032–4039.

Breier, G., et al., "The role of vascular endothelial growth factor in blood vessel formation," Trends in Cell Biology, 1996, 6, 454–456.

Folkman, J., "Angiogenesis in cancer, vascular, rheumatoid and other disease," Nature Medicine, 1995, 1, 27–310.

Parangi, S., et al., "Antiangiogenic therapy of transgenic mice impairs de novo tumor growth," Proc. Natl. Acad. Sci., 1996, 93, 2002–2007.

Aiello, L.P., et al., "Supperssion of retinal neovascularization in vivo, by inhibition of vascular endothelial growth factor (VEGF) using soluble VEGF–receptor chimeric proteins," Proc. Natl. Acad. Sci., 1995, 92, 10457–10461.

Boschelli, D.H., et al., "Synthesis and tyrosine kinase inhibitory activity of a series of 2–amino–8H–pyrido[2,3–d] pyrimidines: identification of potent, selective platelet–derived growth factor receptor tyrosine kinase inhibitors," J. Med. Chem., 1998, 41, 4365–4377.

"The Condensed Chemical Dictionary," Library of Congress Cataloging in Publication Data, Cat. Card No. 76–19024, 1977, p. 25.

Schmidt, H., et al., "A convenient synthesis of 2–substituted 4–amino–5–pyrimidinecarbonitries," Inst. Of Organic Chemistry, 1987, 1305–1307.

* cited by examiner

4,5-DISUBSTITUTED-2-AMINOPYRIMIDINES

This invention relates to certain 4,5-disubstituted-2-aminopyrimidines, to processes for their preparation, to pharmaceutical compositions containing them, and to their use in medicine.

Angiogenesis, the growth of capillaries from existing blood vessels, is an essential process in normal embryonic development, tissue repair and some aspects of female reproductive function. It is also associated with the development of several pathological disorders including solid tumour growth, metastasis, psoriasis and rheumatoid arthritis, as well as diabetic retinopathy and age related macular degeneration (Folkman, Nature Medicine, (1995) 1, 27–310).

Several growth factors have been shown to mediate angiogenesis through alteration of vascular permeability, including vascular endothelial growth factor (VEGF; G. Breier et al., Trends in Cell Biology, 1996, 6, 454–6), platelet derived growth factor (PDGF) and acidic and basic fibroblast growth factors (a & b FGF).

VEGF in dimeric form is a ligand that binds to two transmembrane tyrosine kinase associated receptors, expressed exclusively on proliferating endothelial cells, KDR (Flk-1 in mice) also known as VEGFR-2, and Flt-1 also known as VEGFR-1. Binding of VEGF to KDR/Flk and Flt leads to receptor dimerisation, kinase activation, auto-phosphorylation of the receptor and phosphorylation of intracellular substrates. An analogous series of events ensues after ligand occupancy of the more widely expressed tyrosine kinase associated FGFr receptor by aFGF or bFGF. Thus receptor tyrosine kinase activity initiates a cellular signalling pathway leading to proliferation.

Antagonism of VEGF with antibody completely suppresses neovascularisation and growth of human rhabdomyosarcoma A673 speroids in athymic mice (Borgstrom et al, Cancer Res., 1996, 56 4032–4039). Suppression of bFGF gene expression by interferons α and β inhibits capillary density in mice, leading to pancreatic eyelet tumour suppression (Folkman et al, Proc. Natl. Acad.Sci. 1996, 93, 2002 and Singh et al Proc.Natl. Acad. Sci. 1995, 92, 10457). Other receptor associated kinases such as PDGFβ and EGFr may also have some role in mediating angiogenesis.

We have now found certain 4,5-disubstituted-2-aminopyrimidines which are potent and selective inhibitors of receptor tyrosine kinases involved in angiogenesis, especially KDR kinase and/or FGFr kinase. Selective inhibition of these kinases can be expected to have a beneficial effect and the compounds are thus of use in the prophylaxis and treatment of disease states associated with angiogenesis, as described hereinafter.

Thus, according to one aspect of the invention, we provide a compound of formula (1):

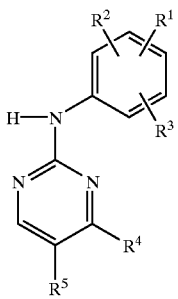

(1)

wherein $R^1$ is a —$XR^6$ group [where X is a covalent bond, —O—, —S—, —C(O)—, —C(S)—, —C(O)O—, —S(O)—, —S(O$_2$)—, —CH$_2$—, or N($R^7$)— [where $R^7$ is a hydrogen atom or a straight or branched alkyl group] and $R^6$ is a hydrogen or halogen atom or an optionally substituted aliphatic, cycloaliphatic, heteroaliphatic, heterocycloaliphatic, aromatic or heteroaromatic group, or a —NO$_2$, —CN, —SO$_2$N($R^8$)($R^9$) [where $R^8$ and $R^9$, which may be the same or different is a hydrogen atom or an optionally substituted aliphatic, cycloaliphatic, heteroaliphatic, heterocycloaliphatic, aromatic or heteroaromatic group], —CON($R^8$)($R^9$), —CSN($R^8$)($R^9$), —NH$_2$ or substituted amino group;

$R^2$ and $R^3$ which may be the same or different is each a hydrogen or halogen atom or a group selected from an optionally substituted aliphatic, cycloaliphatic, heteroaliphatic, heterocycloaliphatic, —OH, —OR$^{10}$ [where $R^{10}$ is an optionally substituted aliphatic, cycloaliphatic, heteroaliphatic, heterocycloaliphatic, aromatic or heteroaromatic group] —SH, —NO$_2$, —CN, —SR$^{10}$, —COR$^{10}$, S(O)R$^{10}$, —SO$_2$R$^8$, —SO$_2$N($R^8$)($R^9$), —CO$_2$R$^8$, —CON($R^8$)($R^9$), —CSN($R^8$)($R^9$), —NH$_2$ or substituted amino group;

$R^4$ is a $X^1R^{11}$ group where $X^1$ is a covalent bond or a —C($R^{12}$)($R^{13}$)— [where each of $R^{12}$ and $R^{13}$ is a hydrogen or halogen atom or a hydroxyl, alkyl or haloalkyl group] or —C(O)— group and $R^{11}$ is an optionally substituted phenyl, thienyl, thiazolyl or indolyl group;

$R^5$ is a halogen atom or an alkynyl group;

and the salts, solvates, hydrates and N-oxides thereof.

In the compounds of formula (1), the term "optionally substituted aliphatic group" when applied to each of the groups $R^2$, $R^3$, $R^6$ and $R^{10}$ means each of these groups may independently be for example an optionally substituted $C_{1-10}$ aliphatic group, for example an optionally substituted straight or branched chain $C_{1-6}$ alkyl, e.g. $C_{1-3}$ alkyl, $C_{2-6}$ alkenyl, e.g. $C_{2-4}$ alkenyl, or $C_{2-6}$ alkynyl, e.g. $C_{2-4}$ alkynyl group. Each of said groups may be optionally interrupted by one or two heteroatoms or heteroatom-containing groups represented by $X^2$ [where $X^2$ is an —O— or —S— atom or a —C(O)—, —C(S)—, —S(O)—, —S(O)$_2$—, —N($R^{14}$)— [where $R^{14}$ is a hydrogen atom or a $C_{1-6}$ alkyl, e.g. methyl or ethyl, group], —CON($R^{14}$)—, —OC(O)N($R^{14}$)—, —CSN($R^{14}$)—, —N($R^{14}$)CO—, —N($R^{14}$)C(O)O—, —N($R^{14}$)CS—, —SON($R^{14}$), —SO$_2$N($R^{14}$), —N($R^{14}$)SO$_2$—, —N($R^{14}$)CON($R^{14}$)—, —N($R^{14}$)CSN($R^{14}$)—, —N($R^{14}$)SON($R^{14}$)— or —N($R^{14}$)SO$_2$N($R^{14}$) group] to form an optionally substituted $R^2$, $R^3$, $R^6$ and $R^{10}$ heteroaliphatic group.

Particular examples of aliphatic groups represented by $R^2$, $R^3$, $R^6$ and/or $R^{10}$ include optionally substituted —CH$_3$, —CH$_2$CH$_3$, —(CH$_2$)$_2$CH$_3$, —CH(CH$_3$)$_2$, —(CH$_2$)$_3$CH$_3$, —CH(CH$_3$)CH$_2$CH$_3$, —CH$_2$CH(CH$_3$)$_2$, —C(CH$_3$)$_3$, —(CH$_2$)$_4$CH$_3$, —(CH$_2$)$_5$CH$_3$, —CHCH$_2$, —CHCHCH$_3$, —CH$_2$CHCH$_2$, —CHCHCH$_2$CH$_3$, —CH$_2$CHCHCH$_3$, —(CH$_2$)$_2$CHCH$_2$, —CCH, —CCCH$_3$, —CH$_2$CCH, —CCCH$_2$CH$_3$, —CH$_2$CCCH$_3$, or —(CH$_2$)$_2$CCH groups. Where appropriate each of said groups may be optionally interrupted by one or two atoms and/or groups $X^2$ to form an optionally substituted heteroaliphatic group. Particular examples include —CH$_2$X$^2$CH$_3$, —CH$_2$X$^2$CH$_2$CH$_3$, —(CH$_2$)$_2$X$^2$CH$_3$ and —(CH$_2$)$_2$X$^2$CH$_2$CH$_3$ groups.

The optional substituents which may be present on these aliphatic and/or heteroaliphatic groups include one, two, three or more substituents selected from halogen atoms, e.g. fluorine, chlorine, bromine or iodine atoms, or hydroxyl, $C_{1-6}$ alkoxy, e.g. methoxy or ethoxy, thiol, $C_{1-6}$ alkylthio e.g. methylthio or ethylthio, —SC(NH)NH$_2$, —CH$_2$C(NH)NH$_2$, amino, substituted amino, cyclic amino or heteroaromatic groups.

Substituted amino groups include for example groups of formulae —NR$^{15}$R$^{16}$ [where R$^{15}$ is an optionally substituted $C_{1-6}$ alkyl, $C_{2-6}$alkenyl or $C_{2-6}$alkynyl group optionally interrupted by one or two heteroatoms or heteroatom-containing groups represented by X$^3$ (where X$^3$ is an atom or group as described above for X$^2$) and R$^{16}$ is a hydrogen atom or is a group as just defined for R$^{15}$], —N(R$^{16}$)COR$^{15}$, —N(R$^{16}$)CSR$^{15}$, —N(R$^{16}$)SOR$^{15}$, —N(R$^{16}$)SO$_2$R$^{15}$, —N(R$^{16}$)CONH$_2$, —N(R$^{16}$)CONR$^{15}$R$^{16}$, —N(R$^{16}$)C(O)OR$^{15}$, —N(R$^{16}$)C(NH)NH$_2$, —N(R$^{16}$)C(NH)NR$^{15}$R$^{16}$, —N(R$^{16}$)CSNH$_2$, —N(R$^{16}$)CSNR$^{15}$R$^{16}$, —N(R$^{16}$)SONH$_2$, —N(R$^{16}$)SONR$^{15}$R$^{16}$, —N(R$^{16}$)SO$_2$NH$_2$, —N(R$^{16}$)SO$_2$NR$^{15}$R$^{16}$, or —N(R$^{16}$)Cyc$^1$ [where Cyc$^1$ is an optionally substituted $C_{3-7}$ monocyclic carbocyclic group optionally containing one or more —O— or —S— atoms or —N(R$^{14}$)—, —C(O)—, —C(S)—, —S(O)— or —S(O$_2$)— groups].

Cyclic amino substituents which may be present on R$^2$, R$^3$, R$^6$ and/or R$^{10}$ aliphatic or heteroaliphatic groups include groups of formula —NHet$^1$, where —NHet$^1$ is an optionally substituted $C_{3-7}$ cyclic amino group optionally containing one or more other heteroatoms or heteroatom containing groups selected from —O— or —S— atoms —N(R$^{14}$)—, —C(O), —C(S)—, —S(O)— or —S(O$_2$)— groups.

Particular examples of amino, substituted amino and cyclic amino groups include —NH$_2$, methylamino, ethylamino, dimethylamino, diethylamino, —NHCyc$^1$ where Cyc$^1$ is an optionally substituted cyclopentyl, cyclohexyl, pyrrolidinyl, imidazolidinyl, pyrazolidinyl, piperidinyl, morpholinyl, piperazinyl or thiomorpholinyl group, or —NHet$^1$ where —NHet$^1$ is an optionally substituted pyrrolidinyl, imidazolidinyl, pyrazolidinyl, piperidinyl, morpholinyl, piperazinyl or thiomorpholinyl group. Optional substituents which may be present on these groups and substituted and cyclic amino groups in general include one, two or three halogen atoms, e.g. fluorine, chlorine, bromine or iodine atoms, or $C_{1-4}$alkyl, e.g. methyl or ethyl, hydroxyl, $C_{1-4}$alkoxy, e.g. methoxy or ethoxy or pyridyl groups.

Optional heteroaromatic substituents which may be present on the aliphatic or heteroaliphatic groups represented by R$^2$, R$^3$, R$^6$ and/or R$^{10}$ include those heteroaromatic groups described below in relation to R$^2$, R$^3$, R$^6$ and R$^{10}$.

When R$^2$, R$^3$, R$^6$ and/or R$^{10}$ is present in compounds of formula (1) as an optionally substituted cycloaliphatic group it may be an optionally substituted $C_{3-10}$ cycloaliphatic group. Particular examples include optionally substituted $C_{3-10}$cycloalkyl, e.g. $C_{3-7}$cycloalkyl, or $C_{3-10}$cycloalkenyl e.g. $C_{3-7}$cycloalkenyl groups.

Heteroaliphatic or heterocycloaliphatic groups represented by R$^2$, R$^3$, R$^6$ and/or R$^{10}$ include the aliphatic or cycloaliphatic groups just described for these substituents but with each group additionally containing one, two, three or four heteroatoms or heteroatom-containing groups represented by X$^2$, where X$^2$ is as described above.

Particular examples of R$^2$, R$^3$, R$^6$ and/or R$^{10}$ cycloaliphatic and heterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, 2,4-cyclopentadien-1-yl, 3,5,-cyclohexadien-1-yl, tetrahydrofuranyl, pyrroline, e.g. 2- or 3-pyrrolinyl, pyrrolidinyl, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, 1,4-dioxanyl, morpholinyl, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1, 4-oxazinyl, 1,2,5-oxathiazinyl, isoxazinyl, oxathiazinyl, e.g. 1,2,5 or 1,2,6-oxathiazinyl, or 1,3,5-oxadiazinyl groups.

Optional substituents which may be present on R$^2$, R$^3$, R$^6$ and/or R$^{10}$ cycloaliphatic and heterocycloaliphatic groups include those optional substituents described above for R$^6$ when it is an aliphatic group. The heterocycloaliphatic groups may be attached to the remainder of the molecule of formula (1) through any appropriate ring carbon or heteroatom.

When R$^2$, R$^3$, R$^6$ and/or R$^{10}$ is present as an aromatic group in compounds of formula (1) it may be for example an optionally substituted monocyclic or bicyclic fused ring $C_{6-12}$ aromatic group, such as an optionally substituted phenyl, 1- or 2-naphthyl, 1- or 2-tetrahydronaphthyl, indanyl or indenyl group.

Heteroaromatic groups represented by R$^2$, R$^3$, R$^6$ and/or R$^{10}$ include optionally substituted $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered fused-ring heteroaromatic groups containing one, two or more heteroatoms selected from oxygen, sulphur or nitrogen atoms.

Examples of heteroaromatic groups represented by R$^2$, R$^3$, R$^6$ and/or R$^{10}$ include optionally substituted pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3, 4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, benzimidazolyl, imidazo[1,2-a]pyridyl, benzothiazolyl, benzoxazolyl, benzopyranyl, [3,4-dihydro]benzopyranyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7, 8-tetrahydroisoquinolinyl, and imidyl, e.g. succinimidyl, phthalimidyl, or naphthalimidyl such as 1,8-naphthalimidyl.

Optional substituents which may be present on any of the just described aromatic or heteroaromatic groups include one, two, three or more substituents, each represented by the group R$^{17}$ as more particularly defined below in relation to the phenyl substituent R$^{11}$.

Substituted amino groups represented by the groups R$^1$, R$^2$ and/or R$^3$ in compounds of formula (1) include for example the groups —NR$^{15}$R$^{16}$, —N(R$^{16}$)COR$^{15}$, —N(R$^{16}$)CSR$^{15}$, —N(R$^{16}$)SOR$^{15}$, —N(R$^{16}$)SO$_2$R$^{15}$, —N(R$^{16}$)CONH$_2$, —N(R$^{16}$)CONR$^{15}$R$^{16}$, —N(R$^{16}$)C(O)OR$^{15}$, —N(R$^{16}$)C(NH)NH$_2$, —N(R$^{16}$)C(NH)NR$^{15}$R$^{16}$, —N(R$^{16}$)CSNH$_2$, —N(R$^{16}$)CSNR$^{15}$R$^{16}$, —N(R$^{16}$)SONH$_2$, —N(R$^{16}$)

$SONR^{15}R^{16}$, $-N(R^{16})SO_2NH_2$, $-N(R^{16})SO_2NR^{15}R^{16}$, $-N(R^{16})Cyc^1$ where $R^{15}$, $R^{16}$ and $Cyc^1$ are as defined above.

Halogen atoms represented by the group $R^5$ in compounds of the invention include fluorine, chlorine, bromine and iodine atoms. Alkynyl groups represented by $R^5$ include —CCH and $CCCH_3$ groups.

The group $R^{11}$ in compounds of formula (1) may be a phenyl or substituted phenyl group. The substituted phenyl group may contain one, two, three or more substituents, each represented by the group $R^{17}$.

The substituent $R^{17}$ may be selected from an atom or group $R^{18}$ or $-Alk(R^{18})_m$, where $R^{18}$ is a halogen atom, or an amino ($-NH_2$), $-NHR^{19}$ [where $R^{19}$ is an $-Alk(R^{18})_m$, heterocycloaliphatic, -Alk-heterocycloaliphatic, aryl or heteroaryl group], $-N(R^{19})_2$ [where each $R^{19}$ group is the same or different], nitro, cyano, hydroxyl (—OH), $-OR^{19}$, formyl, carboxyl ($-CO_2H$), esterified carboxyl, thiol (—SH), $-SR^{19}$, $-COR^{19}$, $-CSR^{19}$, $-SO_3H$, $-SO_2R^{19}$, $-SO_2NH_2$, $-SO_2NHR^{19}$, $SO_2N[R^{19}]_2$, $-CONH_2$, $-CSNH_2$, $-CONHR^{19}$, $-CSNHR^{19}$, $-CON[R^{19}]_2$, $-CSN[R^{19}]_2$, $-N(R^{14})SO_2H$ [where $R^{14}$ is as defined above], $-N(R^{14})SO_2R^{19}$, $-N[SO_2R^{19}]_2$, $-N(R^{14})SO_2NH_2$, $-N(R^{14})SO_2NHR^{19}$, $-N(R^{14})SO_2N[R^{19}]_2$, $-N(R^{14})COR^{19}$, $-N(R^{14})CONH_2$, $-N(R^{14})CONHR^{19}$, $-N(R^{14})CON[R^{19}]_2$, $-N(R^{14})CSR^{19}$, $-N(R^{14})CSNH_2$, $-N(R^{14})CSNHR^{19}$, $-N(R^{14})CSN[R^{19}]_2$, $-N(R^{14})C(O)OR^{19}$, or an optionally substituted cycloaliphatic, heterocycloaliphatic, aryl or heteroaryl group; Alk is a straight or branched $C_{1-6}$ alkylene, $C_{2-6}$ alkenylene or $C_{2-6}$ alkynylene chain, optionally interrupted by one, two or three —O— or —S— atoms or S(O)—, $-S(O)_2$— or $-N(R^{14})$— groups; and m is zero or an integer 1, 2 or 3.

When in the group $-Alk(R^{18})_m$ m is an integer 1, 2 or 3, it is to be understood that the substituent or substituents $R^{18}$ may be present on any suitable carbon atom in -Alk. Where more than one $R^{18}$ substituent is present these may be the same or different and may be present on the same or different atom in -Alk or in $R^{17}$ as appropriate. Thus for example, $R^{17}$ may represent a $-CH(R^{18})_2$ group, such as a —CH(OH)Ar group where Ar is an aryl or heteroaryl group as defined below. Clearly, when m is zero and no substituent $R^{18}$ is present the alkylene, alkenylene or alkynylene chain represented by Alk becomes an alkyl, alkenyl or alkynyl group.

When $R^{18}$ is a halogen atom it may be for example a fluorine, chlorine, bromine, or iodine atom.

Esterified carboxyl groups represented by the group $R^{18}$ include groups of formula $-CO_2Alk^1$ wherein $Alk^1$ is a straight or branched, optionally substituted $C_{1-8}$ alkyl group such as a methyl, ethyl, n-propyl, i-propyl, n-butyl, i-butyl, s-butyl or t-butyl group; a $C_{6-12}arylC_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}aryloxyC_{1-8}$alkyl group such as an optionally substituted phenyloxymethyl, phenyloxyethyl, 1-naphthyloxymethyl, or 2-naphthyloxymethyl group; an optionally substituted $C_{1-8}alkanoyloxyC_{1-8}$alkyl group, such as a pivaloyloxymethyl, propionyloxyethyl or propionyloxypropyl group; or a $C_{6-12}aroyloxyC_{1-8}$alkyl group such as an optionally substituted benzoyloxyethyl or benzoyloxypropyl group. Optional substituents present on the $Alk^1$ group include $R^{18}$ substituents described above.

When Alk is present in or as a substituent $R^{17}$ it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, $-S(O)_2$— or $-N(R^{14})$— groups.

When $R^{18}$ is present in compounds of formula (1) as an optionally substituted cycloaliphatic group it may be an optionally substituted $C_{3-10}$ cycloaliphatic group. Particular examples include optionally substituted $C_{3-10}$cycloalkyl, e.g. $C_{3-7}$cycloalkyl, or $C_{3-10}$cycloalkenyl e.g. $C_{3-7}$cycloalkenyl groups.

Heterocycloaliphatic groups represented by $R^{19}$ and when present $R^{19}$ include the cycloaliphatic groups just described for $R^{18}$ but with each group additionally containing one, two, three or four heteroatoms or heteroatom-containing groups selected from —O— or —S— atoms or $-N(R^{14})$—, —C(O), —C(S)—, —S(O)— or $-S(O_2)$— groups.

Particular examples of $R^{18}$ cycloaliphatic and $R^{18}$ or $R^{19}$ heterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, 2,4-cyclopentadien-1-yl, 3,5,-cyclohexadien-1-yl, tetrahydrofuranyl, pyrroline, e.g. 2- or 3-pyrrolinyl, pyrrolidinyl, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, 1,4-dioxanyl, morpholinyl, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, oxathiazinyl, e.g. 1,2,5 or 1,2,6-oxathiazinyl, or 1,3,5-oxadiazinyl groups.

Optional substituents which may be present on $R^{18}$ cycloaliphatic and $R^{18}$ or $R^{19}$ heterocycloaliphatic groups include one, two, three or more substituents selected from halogen atoms, e.g. fluorine, chlorine, bromine or iodine atoms, or hydroxyl, $C_{1-6}$alkoxy, e.g. methoxy or ethoxy, thiol, $C_{1-6}$alkylthio, e.g. methylthio or ethylthio, hydroxy, $C_{1-6}$alkyl, e.g. hydroxymethyl, hydroxyethyl, —CN, $-NO_2$, $-NHR^{14}$ or $-N(R^{14})_2$ groups.

Aryl and heteroaryl groups represented by the group $R^{18}$ or Ar include for example optionally substituted monocyclic or bicyclic $C_{6-12}$ aromatic groups, e.g. phenyl groups, or $C_{1-9}$ heteroaromatic groups such as those described above in relation to the group $R^6$. Optional substituents which may be present on these groups include one, two or three $R^{18a}$ atoms or groups described below.

Particularly useful atoms or groups represented by $R^{18}$, $-Alk(R^{18})_m$ or $R^{18a}$ as appropriate include fluorine, chlorine, bromine or iodine atoms, or $C_{1-6}$alkyl, e.g. methyl or ethyl, $C_{1-6}$alkylamino, e.g. methylamino or ethylamino, $C_{1-6}$hydroxyalkyl, e.g. hydroxymethyl or hydroxyethyl, $C_{1-6}$alkylthio e.g. methylthiol or ethylthiol, $C_{1-6}$alkoxy, e.g. methoxy or ethoxy, $C_{5-7}$cycloalkoxy, e.g. cyclopentyloxy, halo$C_{1-6}$alkyl, e.g. trifluoromethyl, $C_{1-6}$alkylamino, e.g. methylamino or ethylamino, amino ($-NH_2$), amino$C_{1-6}$alkyl, e.g. aminomethyl or aminoethyl, $C_{1-6}$dialkylamino, e.g. dimethylamino or diethylamino, imido, such as phthalimido or naphthalimido, e.g. 1,8-naphthalimido, 1,1,3-trioxo-benzo[d]-thiazolidino, nitro, cyano, hydroxyl (—OH), formyl [HC(O)—], carboxyl ($-CO_2H$), $-CO_2Alk^1$ [where $Alk^1$ is as defined above], $C_{1-6}$ alkanoyl e.g. acetyl, thiol (—SH), thio$C_{1-6}$alkyl, e.g. thiomethyl or thioethyl, $-SC(NH_2+)NH_2$, sulphonyl ($-SO_3H$), $C_{1-6}$alkylsulphonyl, e.g. methylsulphonyl, aminosulphonyl ($-SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, sulphonylamino (—NHSO$_2$H), C$_{1-6}$alkylsulphonylamino, e.g. methylsulphonylamino or ethylsulphonylamino, C$_{1-6}$dialkylsulphonylamino, e.g. dimethylsulphonylamino or diethylsulphonylamino, optionally substituted phenylsulphonylamino, e.g. 2-, 3- or 4-substituted phenylsulphonylamino such as 2-nitrophenylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, phenylaminosulphonylamino, aminocarbonylamino, C$_{1-6}$alkylaminocarbonylamino e.g. methylaminocarbonylamino or ethylaminocarbonylamino, C$_{1-6}$dialkylaminocarbonylamino, e.g. dimethylaminocarbonylamino or diethylaminocarbonylamino or phenylaminocarbonylamino, C$_{1-6}$alkanoylamino, e.g. acetylamino, optionally substituted phenylcarbonylamino, C$_{1-6}$alkanoylaminoC$_{1-6}$alkyl, e.g. acetylaminomethyl, C$_{1-6}$alkoxycarbonylamino, e.g. methoxycarbonylamino, ethoxycarbonylamino or t-butoxycarbonylamino, optionally substituted heteroC$_{3-6}$cycloalkyl, e.g. piperidinyl, piperazinyl, 4-(C$_{1-6}$alkyl)piperazinyl, e.g. 4-methylpiperazinyl, homopipeprazinyl, or morpholinyl, optionally substituted heteroC$_{3-6}$cycloalkylC$_{1-6}$alkyl, e.g. piperidinylC$_{1-6}$alkyl, piperazinylC$_{1-6}$alkyl, 4-(C$_{1-6}$alkyl)piperazinylC$_{1-6}$alkyl, e.g. 4-methylpiperazinylmethyl, or morpholinyl-C$_{1-6}$alkyl, optionally substituted heteroC$_{3-6}$alkylC$_{1-6}$alkylamino, optionally substituted heteroC$_{3-6}$cycloalkylamino, tetrazolyl, optionally substituted imidazolylC$_{1-6}$alkyl, optionally substituted phenylamino, optionally substituted benzylamino, optionally substituted benzyloxy, or optionally substituted pyridylmethylamino group.

Where desired, two R$^{18}$ or -Alk(R$^{18}$)$_m$ or R$^{18a}$ substituents may be linked together to form a cyclic group such as a cyclic ether, e.g. a C$_{2-6}$alkylenedioxy group such as ethylenedioxy.

It will be appreciated that where two or more R$^{18}$, -Alk(R$^{18}$)$_m$ or R$^{18a}$ substituents are present, these need not necessarily be the same atoms and/or groups.

Especially useful R$^{18}$, -Alk(R$^{18}$)$_m$ or R$^{18a}$ substituents include for example fluorine, chlorine, bromine or iodine atoms, or a methylamino, ethylamino, hydroxymethyl, hydroxyethyl, methylthiol, ethylthiol, methoxy, ethoxy, n-propoxy, 2-hydroxyethoxy, 3-hydroxypropoxy, 4-hydroxybutoxy, 2-amino-ethoxy, 3-aminopropoxy, 2-(methylamino)ethoxy, 2-(dimethylamino)ethoxy, 3-(dimethylamino)propoxy, cyclopentyloxy, cyclohexyl, cyclohexylamino, 2-hydroxycyclohexylamino, trifluoromethyl, trifluoromethoxy, methylamino, ethylamino, amino (—NH)$_2$, aminomethyl, aminoethyl, dimethylamino, diethylamino, ethyl(methyl)amino, propyl(methyl)amino, 2-hydroxyethylamino, 3-hydroxypropylamino, 4-hydroxybutylamino, 2-aminoethylamino, 3-aminopropylamino, 4-aminobutylamino, 2-(methylamino)ethylamino, 2-(ethylamino)ethylamino, 2-(i-propylamino)ethylamino, 3-(i-propylamino)propylamino, 2-(dimethylamino)ethylamino, 3-(dimethylamino)propylamino, 2-(diethylamino)ethylamino, 3-(diethylamino)propylamino, 2-(methylamino)ethyl(methyl)amino, 3-(methylamino)propyl(methyl)amino, 2-(dimethylamino)ethyl(methyl) amino, 2-(dimethylamino)ethyl(ethyl)amino, nitro, cyano, hydroxyl (—OH), formyl [HC(O)—], carboxyl (—CO$_2$H), —CH$_2$CO$_2$H, —OCH$_2$CO$_2$H, —CO$_2$CH$_3$, —CO$_2$CH$_2$CH$_3$, —CH$_2$CO$_2$CH$_3$, —CH$_2$CO$_2$CH$_2$CH$_3$, —CH$_2$CO$_2$CH$_2$phenyl, t-butoxycarbonylmethoxy, acetyl, phenacetyl, thio (—SH), thiomethyl, thioethyl, —SC(NH)NH$_2$, sulphonyl (—SO$_2$H), methylsulphonyl, methylaminosulphonyl, ethylaminosulphonyl, dimethylaminosulphonyl, diethylaminosulphonyl, carboxamido (—CONH$_2$), methylaminocarbonyl, ethylaminocarbonyl, dimethylaminocarbonyl, diethylaminocarbonyl, methylaminocarbonylmethyl, —NHC(S)NH$_2$, sulphonylamino (—NHSO$_2$H), methylsulphonylamino ethylsulphonylamino, dimethylsulphonylamino, diethylsulphonylamino, sulphonylamino (—NHSO$_2$NH$_2$), methylaminosulphonylamino, ethylaminosulphonylamino, dimethylaminosulphonylamino, diethylaminosulphonylamino, methylaminocarbonylamino, ethylaminocarbonylamino, dimethylaminocarbonylamino diethylaminocarbonylamino, acetylamino, phenylcarbonylamino, aminomethylcarbonylamino, acetylaminomethyl, methoxycarbonylamino, ethoxycarbonylamino, t-butoxycarbonylamino, pyrrolidinyl, piperidinyl, piperazinyl, 4-methyl-piperazinyl, homopiperazinyl, morpholinyl, pyrrolidinylC$_{1-6}$alkyl, piperidinylC$_{1-6}$alkyl, piperazinylC$_{1-6}$alkyl, 4-(C$_{1-6}$alkyl)piperazinylC$_{1-6}$akyl, morpholinylC$_{1-6}$alkyl, 2-pyrrolidinylethylamino, 2-(1-methylpyrrolidinyl)-ethylamino, 1-ethylpyrrolidinylmethylamino, piperidinylamino, 1-benzylpiperidinylamino, imidazolylmethyl, imidazolylethyl, 4-(methoxy)phenylamino, 4-(3-hydroxypropyl)phenylamino, benzylamino, benzyloxy or pyridiylmethylamino group.

When X$^1$ is present in compounds of the invention as a —(R$^{12}$)(R$^{13}$)— group it may be for example a —CH$_2$— or —C(R$^{12}$)(R$^{13}$)— group in which R$^{12}$ and/or R$^{13}$ is each a halogen atom such as a fluorine or chlorine atom or a hydroxy, C$_{1-6}$alkyl e.g. methyl, ethyl or i-propyl, or C$_{1-6}$haloalkyl, e.g. trihalomethyl such as a trifluoromethyl group. Particular examples of such —C(R$^{12}$)(R$^{13}$)— groups include —CHF—, —CH(CH$_3$)—, —C(OH)(CF$_3$)— and —CH(CF$_3$)— groups.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, piperazine, dimethylamine or diethylamine salts.

Particularly useful salts of compounds according to the invention include pharmaceutically acceptable salts, especially acid addition pharmaceutically acceptable salts.

It will be appreciated that depending on the nature of the substituents R$^1$, R$^2$, R$^3$ and R$^4$ the compounds of formula (1)

may exist as tautomers and/or geometrical isomers and/or may have one or more chiral centres so that enantiomers or diasteromers may exist. It is to be understood that the invention extends to all such tautomers and isomers of the compounds of formula (1), and to mixtures thereof, including racemates.

In the compounds according to the invention the group $R^4$ is preferably a group $X^1R^{11}$ in which $X^1$ is a covalent bond.

The group $R^5$ in compounds of the invention is in particular a bromine or, especially a chlorine atom.

A particularly useful group of compounds according to the invention has the formula (1a):

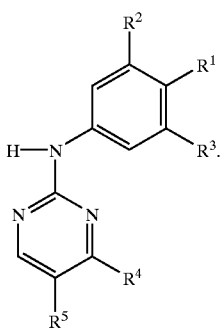

(1a)

wherein $R^1$, $R^2$, $R^3$, $R^4$ and $R^5$ are as defined for formula (1).

One particular class of compounds of formulae (1) and (1a) is that wherein one or both of $R^2$ and $R^3$ is a hydrogen atom. Compounds in which $R^2$ and $R^3$ is each a hydrogen atom are especially useful.

In compounds of this class $R^1$ is in particular a group -(Alk$^2$)$_p$NH$_2$ (where Alk$^2$ is as defined above for Alk and p is zero or an integer 1), -(Alk$^2$)$_p$NR$^{15}$R$^{16}$ (where $R^{15}$ and $R^{16}$ are as defined above), -(Alk$^2$)$_p$NHet$^2$ (where —NHet$^2$ is as defined above for NHet$^1$), -(Alk$^2$)$_p$OH, and -(Alk$^2$)$_p$Ar (where Ar is a nitrogen-containing heteroaromatic group as defined above). Especially useful $R^1$ substituents include -Alk$^2$NH$_2$, particularly —(CH$_2$)$_2$NH$_2$ and —C(CH$_3$)$_2$NH$_2$, -Alk$^2$NR$^{15}$R$^{16}$, particularly —CH$_2$N(CH$_2$CH$_3$)$_2$ and —(CH$_2$)$_2$NHC(CH$_3$)$_3$, -(Alk)$^2_p$NHet$^2$ where —NHet$^2$ is an optionally substituted pyrrolidinyl, piperidinyl, piperazinyl, morpholinyl or thiomorpholinyl group, -Alk$^2$OH, particularly —(CH$_2$)$_2$OH and -(Alk$^2$)$_p$Ar where Ar is an optionally substituted imidazolyl or benzimidazolyl group. Optional substituents which may be present on these particular —NHet$^2$ or Ar groups include those generally and particularly described above in relation to the groups —NHet$^1$ and Ar.

In general in compounds of formulae (1) or (1a) $R^4$ is preferably a group $X^1R^{11}$ in which $X^1$ is a covalent bond and $R^{11}$ is a phenyl or, especially, a substituted phenyl group containing one, two or three $R^{17}$ substituents as defined herein. Particularly useful $R^{17}$ substituents include -(Alk$^2$)$_p$NH$_2$ substituents as just generally and particularly discussed for $R^1$.

Particularly useful compounds according to the invention include:
4-[4-(1-Amino-1-methylethyl)phenyl]-5-chloro-N-[4-(2-hydroxyethyl)phenyl]pyrimidine-2-amine;
4-[4-(1-Amino-1-methylethyl)phenyl]-5-chloro-N-[3-(2-hydroxyethyl)phenyl]pyrimidine-2-amine;
4-[4-(1-Amino-1-methylethyl)phenyl]-5-chloro-N-[4-(1-imidazolyl)phenyl]pyrimidine-2-amine;
4-[4-(1-Amino-1-methylethyl)-3-fluorophenyl]-5-chloro-N-[4-(2-hydroxyethyl)phenyl]pyrimidine-2-amine;
4-[4-(1-Amino-1-methylethyl)phenyl]-5-chloro-N-[4-(2-(imidazol-1-yl)ethyl)phenyl]pyrimidine-2-amine;
4-[4-(1-Amino-1-methylethyl)phenyl]-5-chloro-N-[4-(2-(2-methylimidazol-1-yl)ethyl)phenyl]pyrimidine-2-amine;
4-[4-(1-Amino-1-methylethyl)phenyl]-5-chloro-N-[4-(2-(2-isopropylimidazol-1-yl)ethyl)phenyl]pyrimidine-2-amine;
4-[4-(1-Amino-1-methylethyl)phenyl]-5-chloro-N-[4-(2-thiomorpholino)ethyl)phenyl]pyrimidine-2-amine;
4-[4-(1-Amino-1-methylethyl)phenyl]-5-chloro-N-[4-(2-(tertbutylamino)ethyl)phenyl]pyrimidine-2-amine;
4-[4-(1-Amino-1-methylethyl)phenyl]-5-chloro-N-[4-(2-(4-methylpiperazin-1-yl)ethyl)phenyl]pyrimidine-2-amine;
4-[4-(1-Amino-1-methylethyl)phenyl]-5-chloro-N-[4-(2-(4-ethylpiperazin-1-yl)ethyl)phenyl]pyrimidine-2-amine;
4-[4-(1-Amino-1-methylethyl)phenyl]-5-chloro-N-[4-(2-(3,5-dimethylpiperazin-1-yl)ethyl)phenyl]pyrimidine-2-amine;
4-[4-(1-Amino-1-methylethyl)phenyl]-5-chloro-N-[4-(2-(4-(pyrid-2-yl)piperazin-1-yl)ethyl)phenyl]pyrimidine-2-amine;
4-[4-(1-Amino-1-methylethyl)phenyl]-5-chloro-N-[4-(2-(pyrrolidin-1-yl)ethyl)phenyl]pyrimidine-2-amine;
4-[4-(1-Amino-1-methylethyl)phenyl]-5-chloro-N-[4-(2-(piperidin-1-yl)ethyl)phenyl]pyrimidine-2-amine;
(R)-4-[4-(1-Amino-1-methylethyl)phenyl]-5-chloro-N-[4-(2-(3-dimethylaminopyrrolidin-1-yl)ethyl)phenyl]pyrimidine-2-amine;
and the salts, solvates, hydrates and N-oxides thereof.

Compounds according to the invention are potent and selective inhibitors of KDR and/or FGFr4 kinases as demonstrated by differential inhibition of these enzymes when compared to inhibition of other protein kinases such as EGFr kinase, p56$^{lck}$ kinase, ZAP-70 kinase, protein kinase C, Csk kinase and p59$^{fyn}$ kinase. The ability of the compounds to act in this way may be simply determined by employing tests such as those described in the Examples hereinafter.

The compounds according to the invention are thus of particular use in the prophylaxis and treatment of diseases in which inappropriate KDR kinase action plays a role, for example in disease states associated with angiogenesis. The compounds are then of use for example in the prophylaxis and treatment of cancer, prosiasis, rheumatoid arthritis, Kaposi's Sarcoma, ischemic heart disease, atherosclerosis and occular diseases, such as diabetic retinopathy, involving retinal vessl proliferation and the invention is to be understood to extend to such uses and to the use of a compound of formula (1) in the preparation of a medicament for the prophylaxis and teatment of such diseases.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection, including bolus injection or infusion or particle mediated injection. Formulations for injection may be presented in unit dosage form, e.g. in glass ampoule or multi dose containers, e.g. glass vials or a device containing a compressed gas such as helium for particle mediated administration. The compositions for bolus injection or infusion may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use. For particle mediated administration the complex may be coated on particles such as microscopic gold particles.

In addition to the formulations described above, the compounds of formula (1) may also be formulated as a depot preparation. Such long acting formulations may be administered by implantation or by intramuscular injection. Where desired, the compounds according to the invention may also be conjugated to a polymer, e.g. a naturally occuring polymer such as albumin, to prolong the half life of the compounds when in use. Such conjugates may be formulated and delivered as described above.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $R^1$, $R^2$, $R^3$, $R^4$ and $R^5$ when used in the text or formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) may be prepared by reaction of a guanidine of formula (2):

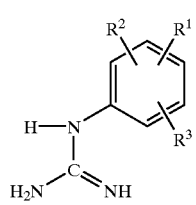

(2)

or a salt thereof
with an enaminone of formula (3):

$$R^4COC(R^5)CHN(R^{20})(R^{21})$$ (3)

where $R^{20}$ and $R^{21}$, which may be the same or different is each a $C_{1-6}$ Alkyl group.

The reaction may be performed in a solvent, for example a protic solvent such as an alcohol, e.g. ethanol, ethoxy-ethanol or propan-2-ol, optionally in the presence of a base e.g. an Alkali metal base, such as sodium hydroxide or potassium carbonate, at an elevated temperature, e.g. the reflux temperature.

Salts of the compounds of formula (2) include acid salts such as inorganic acid salts e.g. hydrochlorides or nitrates.

Intermediate guanidines of formula (2) may be prepared by reaction of the corresponding amine of formula (4):

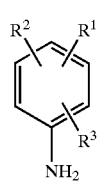

(4)

with cyanamide at an elevated temperature. The reaction may be performed in a solvent such as ethanol at an elevated temperature, e.g. up to the reflux temperature. Where it is desired to obtain a salt of a guanidine of formula (2) the reaction may be performed in the presence of a concentrated acid, e.g. hydrochloric or nitric acid.

The amines of formula (4) are either known compounds or may be obtained by conventional procedures, for example by hydrogenation of the corresponding nitro derivatives using for example hydrogen in the presence of a metal catalyst in a suitable solvent, for example as more particularly described in the interconversion reactions discussed below. The nitrobenzenes for this particular reaction are either known compounds or may be prepared using similar methods to those used for the preparation of the known compounds.

Intermediate enaminones of formula (3) are either known compounds or may be prepared by reaction of an acetyl derivative $R^4COCH_2R^5$ with an acetal $(R^{20})(R^{21})NCH(OR^{22})_2$ (where $R^{22}$ is a $C_{1-6}$Alkyl group such as a methyl or ethyl group) at an elevated temperature. The starting materials for this reaction are either known compounds or may be prepared by methods analogous to those used for the preparation of the known compounds.

In another process according to the invention, a compound of formula (1) may be prepared by displacement of a chlorine atom in a pyrimidine of formula (5):

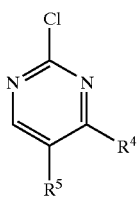

(5)

with an amine of formula (4)

The reaction may be performed at an elevated temperature, for example the reflux temperature, where necessary in the presence of a solvent, for example an alcohol, such as 2-ethoxyethanol or isopopanol, a cyclic ether, e.g. dioxane or a substituted amide such as dimethylformamide, optionally in the presence of a base, for example an organic amine such as pyridine.

Intermediate pyrimidines of formula (5) may be obtained by reaction of a corresponding pyrimidine of formula (6):

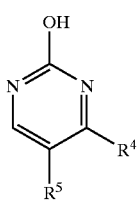

(6)

with phosphorous oxychloride optionally in a solvent such as a substituted amide e.g. dimethylformamide at an elevated temperature, for example the reflux temperature.

Intermediates of formula (6) may be prepared from the corresponding amine of formula (7):

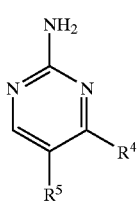

(7)

with sodium nitrite in an aqueous acid,e.g. aqueous sulphuric acid at around ambient temperature.

Amines of formula (7) may be prepared by reaction of an enaminone of formula (3) with a guanidine salt, e.g. guanidine carbonate, as described above for the preparation of compounds of formula (1).

Compounds of formula (1) may also be prepared by interconversion of other compounds of formula (1) and it is to be understood that the invention extends to such interconversion processes. Thus, for example, standard substitution approaches employing for example Alkylation, arylation, heteroarylation, acylation, thioacylation, sulphonylation, formylation or coupling reactions may be used to add new substitutents to and/or extend existing substituents in compounds of formula (1). Alternatively existing substituents in compounds of formula (1) may be modified by for example oxidation, reduction or cleavage reactions to yield other compounds of formula (1).

The following describes in general terms a number of approaches which can be employed to modify existing phenyl and/or other aromatic of heteroaromatic groups in compounds of formula (1). It will be appreciated that each of these reactions will only be possible where an appropriate functional group exists in a compound of formula (1). Where desired, these reactions may also be performed on intermediates to compounds of formula (1).

Thus, for example Alkylation, arylation or heteroarylation of a compound of formula (1) may be achieved by reaction of the compound with a reagent Alk, L or ArL, where Alk is an Alkyl group and Ar is an aryl or heteroaryl group as defined above in relation to compounds of formula (1) and L is a leaving atom or group such as a halogen atom, e.g. a chlorine or bromine atom, or a sulphonyloxy group, e.g. an arylsulphonyloxy group such as a p-toluenesulphonyloxy group.

The Alkylation or arylation reaction may be carried out in the presence of a base, e.g. an inorganic base such as a carbonate, e.g. caesium or potassium carbonate, an Alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at around 0° C. to around 40° C.

In a variation of this process the leaving group L may be alternatively part of the compound of formula (1) and the reaction performed with an appropriate nucleophilic reagent at an elevated temperature. Particular nucleophilic reagents include cyclic amines, such as piperazine. Where appropriate the reaction may be performed in a solvent such as an aprotic solvent, e.g. a substituted amide such as dimethylformamide.

In another general example of an interconversion process, a compound of formula (1) may be acylated or thioacylated. The reaction may be performed for example with an acyl halide or anhydride in the presence of a base, such as a tertiary amine e.g. triethylamine in a solvent such as a halogenated hydrocarbon, e.g. dichloromethane at for example ambient temperature, or by reaction with a thioester in an inert solvent such as tetrahydrofuran at a low temperature such as around 0° C. The reaction is particularly suitable for use with compounds of formula (1) containing primary or secondary amino groups.

In a further general example of an interconversion process, a compound of formula (1) may be formylated, for example by reaction of the compound with a mixed anhydride $HCOOCOCH_3$ or with a mixture of formic acid and acetic anhydride.

Compounds of formula (1) may be prepared in another general interconversion reaction by sulphonylation, for example by reaction of the compound with a reagent $AlkS(O)_2L$, or $ArS(O)_2L$ in the presence of a base, for example an inorganic base such as sodium hydride in a solvent such as an amide, e.g. a substituted amide such as dimethylformamide at for example ambient temperature. The reaction may in particular be performed with compounds of formula (1) possessing a primary or secondary amino group.

In further examples of interconversion reactions according to the invention compounds of formula (1) may be prepared from other compounds of formula (1) by modification of existing functional groups in the latter.

Thus in one example, ester groups —$CO_2Alk^1$ in compounds of formula (1) may be converted to the corresponding acid [—$CO_2H$] by acid- or base-catalysed hydrolysis or by catalytic hydrogenation depending on the nature of the group $Alk^1$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an Alkali metal hydroxide, e.g. lithium hydroxide in an aqueous alcohol, e.g. aqueous methanol. Catalytic hydrogenation may be carried out using for example hydrogen in the presence of a metal catalyst, for example palladium on a support such as carbon in a solvent such as an ether, e.g. tetrahydrofuran or an alcohol, e.g. methanol.

In a second example, —OAlk [where Alk represents an Alkyl group such as a methyl group] groups in compounds of formula (1) may be cleaved to the corresponding alcohol —OH by reaction with boron tribromide in a solvent such as a halogenated hydrocarbon, e.g. dichloromethane at a low temperature, e.g. around −78° C.

In another example, alcohol —OH groups in compounds of formula (1) may be converted to a corresponding —OAlk or —OAr group by coupling with a reagent AlkOH or ArOH in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NH_2$] groups in compounds of formula (1) may be obtained, in another example, by reaction of a corresponding amine [—$NH_2$] with sulphamide in the presence of an organic base such as pyridine at an elevated temperature, e.g. the reflux temperature.

In another example of an interconversion process secondary amine groups in compounds of formula (1) may be Alkylated using an alcohol, e.g. ethanol and catalytic hydrogenation, employing for example hydrogen in the presence of a metal catalyst such as palladium on a support such as carbon.

In a further example, amine [—$NH_2$] groups in compounds of formula (1) may be obtained by hydrolysis from a corresponding imide by reaction with hydrazine in a solvent such as an alcohol, e.g. ethanol at ambient temperature. In an alternative, amine groups may also be generated by reduction of the corresponding nitrile, for example using a reducing agent such as a borohydride, e.g. sodium borohydride or cerium trichloride.

In another example, a nitro [—$NO_2$] group may be reduced to an amine [—$NH_2$], for example by catalytic hydrogenation as just described, or by chemical reduction using for example a metal, e.g. tin or iron, in the presence of an acid such as hydrochloric acid.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Where salts of compounds of formula (1) are desired, these may be prepared by conventional means, for example by reaction of a compound of formula (1) with an appropriate acid or base in a suitable solvent or mixture of solvents, e.g. an organic solvent such as an ether, e.g. diethylether, or an alcohol, e.g. ethanol.

The following Examples illustrate the invention. In the Examples all $^1$Hnmr were run at 300 MHz unless specified otherwise. All temperatures are in ° C.

The following abbreviations are used:
THF—tetrahydrofuran;
DMSO—dimethylsulphoxide;
DMF—dimethylformamide;
TFA—trifluoroacetic acid;

EXAMPLE 1

4-[4-(1-Amino-1-methylethyl)phenyl]-5-chloro-N-[4-(2-hydroxyethyl)phenyl]pyrimidine-2-amine A mixture of 4-[4-(1-tertbutoxycarbonylamino-1-methylethyl)phenyl]-2,5-dichloropyrimidine (1.53 g, 4.0 mmol) and 4-aminophenethyl alcohol (1.10 g, 8.0 mmol) in 2-ethoxyethanol (15 ml) was heated to reflux for 18 h. The reaction was cooled to room temperature, trifluoroacetic acid (2 ml) added and the reaction stirred for 30 min. Solvent was removed in vacuo and the residue partitioned between $CH_2Cl_2$ (100 ml) and saturated, aqueous $Na_2CO_3$ (80 ml). The aqueous layer was re-extracted with $CH_2Cl_2$ (2×80 ml) and the combined $CH_2Cl_2$ layer washed with aqueous $Na_2CO_3$ (80 ml), brine (80 ml), dried ($MgSO_4$) and concentrated in vacuo. The crude product was purified by column chromatography (silica, 10–15% methanol in $CH_2Cl_2$) to give the title compound as a buff solid (1.30 g) m.p. 162–163°. δH ($d^6$DMSO) 9.74 (1H, s), 8.55 (1H, s), 7.76 (2H, d, J 8.5 Hz), 7.68 (2H, d, J 8.5 Hz), 7.62 (2H, d, J 8.5 Hz), 7.12 (2H, d, J 8.5 Hz), 4.57 (1H, bs), 3.55 (2H, m), 2.65 (2H, t, J 7.2 Hz), 1.41 (6H, s); MS (ESI) 383 (MH$^+$, $^{35}$Cl, 100%).

The 4-[4-(1-tertbutoxycarbonylamino-1-methylethyl)phenyl]-2,5-dichloro pyrimidine used in the above process was prepared as follows:

Cerium trichloride heptahydrate (22.47 g, 60 mmol) was dried in a flask under high vacuum (0.08 Torr) heated by an oil bath at 140–160° for 4 h. On cooling, nitrogen was introduced slowly into the flask and anhydrous THF (120 ml) added to give a suspension of $CeCl_3$ which was stirred for 16 h at room temperature. The mixture was cooled to −65°, methyl lithium (37.5 ml of a 1.6M solution in diethylether, 60 mmol) added dropwise and the mixture stirred for 0.5 h. A solution of 4-bromobenzonitrile (3.64 g, 20 mmol) in THF (10 ml) was added and the reaction stirred at −65° for 3.5 h before allowing the mixture to warm to −40°. The reaction was quenched by the addition of 33% ammonium hydroxide (50 ml) and then allowed to warm to room temperature. The resulting solids were removed by filtration through a pad of Celite® and were washed with ethyl acetate (3×100 ml). The combined filtrates were washed with brine (20 ml), the organic phase dried ($MgSO_4$) and concentrated in vacuo to give 1-(4-bromophenyl)-1-methylethylamine as a yellow oil (4.01 g). This product was heated at reflux in toluene (40 ml) with di-tert-butyl dicarbonate (4.50 g, 20.6 mmol) for 1 h. Solvent was removed in vacuo and the crude product recrystallised from hexane at −20° to give tertbutyl N-{1-(4-bromophenyl)-1-methylethyl}carbamate as colourless crystals (3.47 g) m.p. 92–93° δH (CDCl$_3$) 7.43 (2H, dt, J 8.7, 2.7 Hz), 7.26 (2H, dt, J 8.8, 2.6 Hz), 4.91 (1H, bs), 1.59 (6H, s), 1.36 (9H, bs).

A mixture of tert-butyl N-{1-(4-bromophenyl)-1-methylethyl}carbamate (1.57 g, 5.0 mmol), bis(pinacolato)

diboron (1.40 g, 5.5 mmol), [1,1'-bis(di-phenylphosphino) ferrocene]dichloropalladium(II) (123 mg, 0.015 mmol) and potassium acetate (1.47 g, 15.0 mmol) was dissolved in dry DMF (20 ml) under nitrogen and heated to 80° for 5 h. The reaction was then concentrated under reduced pressure, the resulting residue taken up in dichloromethane (80 ml) and washed with water (1×80 ml), then brine (1×80 ml), dried (MgSO$_4$) and again concentrated. The residue was subjected to column chromatography (silica gel; 15% ethyl acetate-hexane) to give tert-butyl N-{1-[4-(4,4,5,5-tetramethyl-1,3, 2-dioxaborolan-2-yl)phenyl]-1-methylethyl}carbamate (1.55 g) as a white solid m.p. 140°. δH (CDCl$_3$) 7.77 (2H, d, J 8.3 Hz), 7.40 (2H, d, J 8.4 Hz), 1.63 (6H, s) and 1.34 (21H, s).

2M aqueous Na$_2$CO$_3$ (4.7 ml, 9.4 mmol) was added to a solution of 2,4,5-trichloropyrimidine [Chesterfield, J.; McOmie, J. F. W.; Sayer, E. R.; J. Chem. Soc. (1955) 3478–3481] (1.18 g, 6.44 mmol), tert-butyl N-{1-[4-(4,4,5, 5-tetramethyl-1,3,2-dioxaborolan-2-yl)phenyl]1-methylethyl}carbamate (1.55 g, 4.29 mmol) and tetrakis (triphenylphosphine)palladium (O) (150 mg, 0.13 mmol) in ethyleneglycol dimethylether (20 ml) under N$_2$ and the mixture heated to reflux for 6 h. The reaction was diluted with H$_2$O (30 ml) and extracted with ethyl acetate (3×50 ml), the combined ethyl acetate extracts were washed with brine (30 ml), dried (MgSO$_4$) and concentrated in vacuo. The crude product was purified by column chromatography (SiO$_2$, 15% ethyl acetate in hexane) to give 4-[4-(1-tert-butoxycarbonylamino-1-methylethyl)phenyl]-2,5-dichloropyrimidine as a white solid (1.34 g). δH (d$^6$DMSO) 8.62 (1H, s), 7.90 (2H, d, J 8.6 Hz), 7.54 (2H, dt, J 8.7, 2.1 Hz), 5.02 (1H, bs), 1.65 (6H, s) and 1.37 (9H, s).

EXAMPLE 2

4-[4-(1-Amino-1-methylethyl)phenyl]-5-chloro-N-[3-(2-hydroxyethyl)phenyl]pyrimidine-2-amine The title compound was prepared from 4-[4-(1-tert-butoxycarbonylamino-1-methylethyl)phenyl]-2,5-dichloropyrimidine (1.50 g, 6.55 mmol) and 2-(3-aminophenyl)ethanol (942 mg, 6.87 mmol) following the method of Example 1. The crude product was purified by chromatography (Silica, 10% methanol in CH$_2$Cl$_2$) to give the title compound as a brown solid (600 mg) m.p. 184–185°. δH (d$^6$DMSO) 9.77 (1H, s), 8.57 (1H, s), 7.79 (2H, d, J 8.4 Hz), 7.68 (2H, d, J 8.4 Hz), 7.61–7.58 (2H, m), 7.17 (1H, t, J 7.7 Hz), 6.82 (1H, d, J 7.4 Hz), 4.62 (1H, bs), 3.60 (2H, t, J 7.0 Hz), 2.68 (2H, t, J 7.1 Hz), 2.07 (2H, bs), 1.41 (6H, s); MS (ESI) 383 (MH$^+$, $^{35}$Cl).

EXAMPLE 3

4-[4-(1-Amino-1-methylethyl)phenyl]-5-chloro-N-[4-(1-imidazolyl)phenyl]pyrimidine-2-amine Sodium hydride (330 mg, 8.25 mmol) was added to a solution of 4-[4-(1-tert-butoxycarbonylamino-1-methylethyl)phenyl]-2,5-dichloropyrimidine (1.0 g, 2.62 mmol) and 1-(4-aminophenyl)-1H-imidazole (438 mg, 2.75 mmol) in dry THF (40 ml) under N$_2$ and the mixture heated to reflux for 3 h. The reaction was quenched with H$_2$O (5 ml), diluted with brine (50 ml) and extracted with ethyl acetate (2×150 ml). The ethyl acetate extracts were dried (MgSO$_4$), concentrated in vacuo and the residue purified by column chromatography (silica; 2% ethyl acetate in CH$_2$Cl$_2$) to give 4-[4-(1-tert-butoxy carbonylamino-1-methylethyl) phenyl]-5-chloro-N-[4-(1-imidazolyl)-phenyl]pyrimidine-2-amine as a yellow solid (310 mg) m.p. 218–220°. This intermediate was stirrd at room temperature in trifluoroacetic acid (4 ml) for 3 h before concentrating the reaction in vacuo. The residue was diluted with 2M NaOH (aq) (50 ml) and extracted with CH$_2$Cl$_2$-ethanol (20:1) (3×50 ml), the extracts dried (MgSO$_4$) and concentrated in vacuo. Trituration of the resultant solid with diethylether-ethyl acetate (4:1) gave the title compound as a pale yellow solid (175 mg) m.p. 199–201°. δH (d$^6$DMSO) 10.05 (1H, bs), 8.62 (1H, s),8.15 (1H, s), 7.88 (2H, d, J 7.9 Hz), 7.78 (2H, d, J 8.5 Hz), 7.69 (2H, d, J 8.5 Hz), 7.65 (1H, s), 7.55 (2H, d, J 8.8 Hz), 1.42 (6H, s). MS (ESI) 405 (MH$^+$, 100%).

1-(4-Aminophenyl)-1H-imidazole used in the above process was prepared by suspending 1-(4-nitrophenyl)-1H-imidazole (10.0 g, 52.86 mmol) and 10% Pd on carbon (1 g) in ethanol (125 ml). The mixture was degassed with N$_2$ and subjected to an atmosphere of hydrogen (balloon) for 24 h at room temperature with magnetic stirring. The reaction was filtered through Celite®, washing the filter cake with ethanol (125 ml) and the filtrates concentrated in vacuo to give 1-(4-aminophenyl)-1H-imidazole as an off white solid (8.02 g) m.p. 156–157°.

EXAMPLE 4

4-[4-(1-Amino-1-methylethyl)-3-fluorophenyl]-5-chloro-N-[4-(2-hydroxyethyl)phenyl]pyrimidine-2-amine The title compound was prepared from 4-[4-(1-tert-butoxycarbonylamino-1-methylethyl)-3-fluorophenyl]-2,5-dichloropyrimidine (1.60 g, 4.0 mmol) and 4-aminophenethyl alcohol (826 mg, 6.0 mmol) following the method of Example 1.

The crude product was purified by column chromatography (silica; 5–10% MeOH in CH$_2$Cl$_2$) to give the title compound as a light brown solid (920 mg) m.p. 172–176°. δH (CDCl$_3$) 8.43 (1H, s), 7.67 (1H, dd, J 8.2, 1.8 Hz), 7.62–7.55 (4H, m), 7.22 (2H, d, J 8.5 Hz), 7.19 (1H, bs), 3.86 (2H, t, J 6.5 Hz), 2.86 (2H, t, J 6.5 Hz), 1.68 (2H, bs), 1.60 (6H, s). MS (ESI) 401 (MH$^+$).

The intermediate 4-[4-(1-tertbutoxycarbonylamino-1-methylethyl)-3-fluoro-phenyl]-2,5-dichloropyrimidine in the above process was prepared using the same methods described for its analogue in Example 1. Thus starting from 4-bromo-2-fluorobenzonitrile the following intermediates were prepared:

tert-Butyl N-{1-(4-bromo-2-fluorophenyl)-1-methylethyl}carbamate as an off white solid δH (CDCl$_3$) 7.25–7.16 (3H, m), 4.98 (1H, bs), 1.66 (6H, s), 1.36 (9H, bs).

tert-Butyl N-{1-[4-(4,4,5,5-tetramethyl-1,3,2-dioxanborolan-2-yl)-2-fluorophenyl]-1-methylethyl}carbamate as a white solid δH (CDCl$_3$) 7.51 (1H, dd, J 7.7, 1.1 Hz), 7.42 (1H, dd, J 13.0, 1.1 Hz), 7.34 (1H, t, J 8.0 Hz), 5.01 (1H, bs), 1.68 (6H, s), 1.33 (21H, bs).

4-[4-(1-tertButoxycarbonylamino-1-methylethyl)-3-fluorophenyl]-2,5-dichloropyrimidine m.p. 148–149°. δH (CDCl$_3$) 8.65 (1H, s). 7.72 (1H, dd, J 8.3, 1.9 Hz), 7.64 (1H, dd, J 13.1, 1.8 Hz), 7.50 (1H, t, J 8.3 Hz), 5.04 (1H, bs), 1.72 (6H, s), 1.37 (9H, s) MS (ESI) 422 (MNa$^+$).

EXAMPLE 5

4-[4-(1-Allyloxycarbonylamino-1-methylethyl) phenyl]-5-chloro-N-[4-(2-(imidazol-1-yl)ethyl) phenyl]pyrimidine-2-amine p-Toluenesulphonyl chloride (867 mg, 4.55 mmol) was added to a solution of 4-[4-(1-allyloxycarbonylamino-1-methylethyl)phenyl-5-chloro-N-[4-(2-hydroxyethyl)phenyl] pyrimidine-2-amine (1.16 g, 3.03 mmol), pyridine (2.45 ml, 30.3 mmol) and 4-dimethylaminopyridine (50 mg) in $CH_2Cl_2$ (25 ml). The reaction was stirred at room temperature under $N_2$ for 18 h before diluting with $CH_2Cl_2$ (50 ml). The dichloromethane solution was washed with 2M hydrochloric acid (2×80 ml), brine (80 ml), dried ($MgSO_4$) and concentrated in vacuo to give a thick oil. Column chromatography (silica; 35% ethyl acetate in hexane) gave 4-[4-(1-allyloxycarbonylamino-1-methylethyl)phenyl]-5-chloro-N-[4-(2-ptoluenesulphonyloxyethyl)phenyl]pyrimidine-2-amine as a pale yellow solid (1.40 g). $\delta$H ($CDCl_3$) 8.42 (1H, s), 7.89 (2H, d, J 8.5 Hz), 7.70 (2H, dt, J 8.4, 1.8 Hz), 7.56–7.51 (5H, m), 7.28 (2H, d, J 8.6 Hz), 7.09 (2H, d, J 8.5 Hz), 5.90 (1H, bs), 5.32 (1H, bs), 5.21 (2H,s), 4.51 (2H, d, J 5.5 Hz), 4.20 (2H, t, J 7.1 Hz), 2.93 (2H, t, J 7.1 Hz), 2.41 (3H,s), 1.71 (6H, s).

To the tosylate prepared above (1.0 g, 1.61 mmol) in dry DMF (20 ml) under $N_2$ was added imidazole (1.03 g, 15.2 mmol) and the mixture heated to 80° for 18 h. Solvent was removed in vacuo and the residue dissolved in $CH_2Cl_2$ (80 ml), washed with aqueous $Na_2CO_3$ (3×20 ml), brine (20 ml), dried ($MgSO_4$) and concentrated in vacuo. Column chromatography (silica; 5% methanol in $CH_2Cl_2$) gave 4-[4-(1-allyloxycarbonylamino-1-methylethyl) phenyl]-5-chloro-N-[4-(2-imidazol-1-ylethyl)phenyl]pyrimidine-2-amine as a yellow solid (670 mg) m.p. 72–78°. $\delta$H ($CDCl_3$) 8.41 (1H, s) 7.88 (2H, d, J 8.6 Hz), 7.61–7.52 (4H, m), 7.35 (1H, bs), 7.21 (2H, d, J 8.5 Hz), 5.89 (1H, bs), 5.39–5.13 (3H, m), 4.50 (2H, d, J 5.6 Hz), 3.86 (2H, t, J 6.5 Hz), 2.85 (2H, t, J 6.5 Hz), 1.71 (6H, s). MS (ESI) 517 (MH+, 100%).

The intermediate 4-[4-(1-allyloxycarbonylamino-1-methylethyl)phenyl-5-chloro-N-[4-(2-hydroxy-ethyl)phenyl]pyrimidine-2-amine used in the above process was prepared as follows:

To a solution of the compound of Example 1 (1.20 g, 3.1 mmol) in $CH_2Cl_2$ (40 ml) was added saturated, aqueous $Na_2CO_3$ (20 ml) and allylchloroformate (410 mg, 3.4 mmol) and the reaction stirred at room temperature for 2 h. The $CH_2Cl_2$ layer was separated, dried ($MgSO_4$) and concentrated in vacuo. The crude material was purified by column chromatography (silica; 5% methanol in $CH_2Cl_2$) to give the desired intermediate as a yellow solid (1.23 g). $\delta$H ($CDCl_3$) 8.41 (1H, s), 7.88 (2H, d, J 8.6 Hz), 7.61–7.51 (4H, m), 7.35 (1H, bs), 7.21 (2H, d, J 8.5 Hz), 6.91 (1H, bs) 5.40–5.18 (3H, m), 4.50 (2H, d, J 5.6 Hz), 3.86 (2H, t, J 6.5 Hz), 2.85 (2H, t, J 6.5 Hz), 1.71 (6H, s). MS (ESI) 467 (MH+, 100%).

EXAMPLE 6

4-[4-(1-Allyloxycarbonylamino-1-methylethyl) phenyl]-5-chloro-N-[4-(2-morpholinoethyl)phenyl] pyrimidine-2-amine A mixture of the tosylate prepared in Example 5 (400 mg, 0.64 mmol) and morpholine (0.28 ml, 3.22 mmol) was heated to reflux in dry THF (10 ml) under $N_2$ for 18 h. The reaction was diluted with ethyl acetate (40 ml), washed with saturated, aqueous $Na_2CO_3$ (2×20 ml), dried ($MgSO_4$) and concentrated in vacuo. The crude product was purified by column chromatography (4% methanol in $CH_2Cl_2$) to give the title compound as a yellow solid (310 mg) m.p. 65–69° $\delta$H ($CDCl_3$) 8.41 (1H, s) 7.88 (2H, d, J 8.5 Hz), 7.57–7.52 (4H, m), 7.19 (2H, d, J 8.4 Hz), 7.18 (1H, obscured by over-lapping signal), 5.88 (1H, bs), 5.36–5.19 (3H, m), 4.50 (2H, d, J 5.6 Hz), 3.85 (4H, bs), 3.06–2.43 (8H, m), 1.71 (6H, s).

EXAMPLE 7

4-[4-(1-Allyloxycarbonylamino-1-methylethyl)-3-fluorophenyl]-5-chloro-N-[4-(2-(imidazol-1-yl) ethyl)phenyl]pyrimidine-2-amine The title compound was prepared from 4-[4-(1-allyloxycarbonylamino-1-methylethyl)-3-fluorophenyl]-5-chloro-N-[4-(2-p-toluenesulphonyloxyethyl)-phenyl] pyrimidine-2-amine (504 mg, 0.79 mmol) and imidazole (337 mg, 4.95 mmol) following the method described for Example 5. The crude product was purified by column chromatography (silica; 5% methanol in $CH_2Cl_2$) to give the title compound as a yellow solid (330 mg) m.p. 88° forms gum. $\delta$H ($CDCl_3$) 8.43 (1H, s), 7.69 (1H, dd, J 8.2, 1.8 Hz), 7.61 (1H, dd, J 13.3, 1.8 Hz), 7.54 (2H, d, with fine splitting, J 8.6 Hz), 7.50 (1H, t, J 8.5 Hz), 7.34 (1H, s), 7.18 (1H, s), 7.04 (3H, m), 5.89 (1H, bs), 5.30–5.12 (3H, m), 4.50 (2H, dt, J 5.6, 1.4 Hz), 4.16 (2H, t, J 7.1 Hz), 3.03 (2H, t, J 7.0 Hz), 1.78 (6H, s); MS (ESI) 535 (MH+, 100%).

The intermediate tosylate used in the above process was prepared using the same methods described for its analogue in Example 5: thus starting from the compound of Example 4 the following intermediates were prepared:

4-[4-(1-Allyloxycarbonylamino-1-methylethyl)-3-fluorophenyl-5-chloro-N-[4-(2-hydroxyethyl)phenyl] pyrimidine-2-amine as a yellow solid. $\delta$H ($CDCl_3$) 8.42 (1H, s), 7.69 (1H, d, J 8.2 Hz), 7.61 (1H, d, J 13.4 Hz), 7.56 (2H, d, J 8.4 Hz), 7.49 (1H, t, J 8.4 Hz), 7.22 (2H, d, J 8.5 Hz), 7.21 (1H, bs), 5.88 (1H, bs), 5.30 (1H, s), 5.29–5.16 (2H, m), 4.49 (2H, m), 3.86 (2H, t, J 6.3 Hz), 2.86 (2H, t, J 6.3 Hz), 1.78 (6H, s); MS (ESI) 485 (MH+, 100%).

4-[4-(1-Allyloxycarbonylamino-1-methylethyl)-3-fluorophenyl]-5-chloro-N-[4-(2-ptoluenesulphonyloxyethyl)phenyl]pyrimidine-2-amine as a yellow solid. $\delta$H ($CDCl_3$) 8.43 (1H, s), 7.70 (4H, m), 7.62 (1H, dd, J 13.3, 1.8 Hz), 7.54–7.48 (3H, m), 7.29 (2H, d, J 8.0 Hz), 7.10 (2H, d, J 8.5 Hz), 5.88 (1H, bs), 5.33–5.12 (3H, m), 4.51 (2H, m), 4.20 (2H, t, J 7.1 Hz), 2.94 (2H, t, J 7.0 Hz), 2.42 (3H, s), 1.78 (6H, s).

EXAMPLE 8

4-[4-(1-Amino-1-methylethyl)phenyl]-5-chloro-N-[4-(2-imidazol-1-yl)ethyl)phenyl]pyrimidine-2-amine Tetrakis(triphenylphosphine)palladium(O)(147 mg, 0.13 mmol) was added to a solution of the compound of Example 5 (655 mg, 1.27 mmol) and 5,5-dimethyl-1,3-cyclohexanedione (1.42 g, 10.15 mmol) in anhydrous THF (20 ml) under $N_2$. The reaction was stirred for 30 min at room temperature and was then diluted with ethyl acetate (50 ml), washed with 2M aqueous NaOH (3×20 ml), brine (20 ml), dried ($MgSO_4$) and concentrated in vacuo. The crude product was purified by column chromatography (Silica; 10% methanol in $CH_2Cl_2$) to give the title compound as a yellow solid (380 mg). $\delta$H ($CDCl_3$) m 8.41 (1H, s), 7.86 (2H, d, J 8.5 Hz), 7.64 (2H, d, J 8.5 Hz), 7.55 (2H, d, J 8.5 Hz), 7.36 (1H, bs), 7.34 (1H, bs), 6.99 (3H, m), 6.83 (1H, bs), 4.14 (2H, m), 3.00 (2H, t, J 7.0 Hz), 2.72 (2H, bs), 1.57 (6H, s). MS (ESI) 433 (MH+, 100%).

The following examples 9 and 10 were prepared by the method described for Example 8.

EXAMPLE 9

4-[4-(1-Amino-1-methylethyl)phenyl]-5-chloro-N-[4-(2-morpholinoethyl)phenyl]pyrimidine-2-amine From the compound of Example 6 (310 mg, 0.58 mmol), tetrakis-(triphenylphosphine)palladium(O) (60 mg, 0.06 mmol) and 5,5-dimethyl-1,3-cyclohexadione (650 mg, 4.64 mmol) to give the title compound as a pale yellow solid (240 mg) m.p. 166–173° δH (CDCl$_3$) 8.40 (1H, s), 7.87 (2H, d, J 8.4 Hz), 7.65 (2H, d, J 8.3 Hz), 7.53 (2H, d, J 8.3 Hz), 7.24 (1H, bs), 7.17 (2H, d, J 8.4 Hz), 3.75 (4H, m), 2.78 (2H, m), 2.58 (8H, m), 1.58 (6H, s). MS (ESI) 452 (MH+).

EXAMPLE 10

4-[4-(1-Amino-1-methylethyl)-3-fluorophenyl]-5-chloro-N-[4-(2-(imidazol-1-yl)ethyl)phenyl]pyrimidine 2-amine From the compound of Example 7 (330 mg, 0.62 mmol) tetrakis-(triphenylphosphine)palladium(O) (71 mg, 0.062 mmol) and 5,5-dimethyl-1,3-cyclohexadione (692 mg, 4.94 mmol) to give after chromatography (Silica; 8% methanol in CH$_2$Cl$_2$) the title compound as a yellow solid (200 mg) m.p. 112–120° δH (d$^6$ DMSO) 9.85 (1H, s), 8.60 (1H, s), 7.77 (1H, t, J 8.4 Hz), 7.62 (2H, d, J 8.5 Hz), 7.57 (1H, s, with fine splitting), 7.52 (1H, d, J 1.7Hz), 7.48 (1H, s), 7.12 (1H, s), 7.08 (2H, d, J 8.5 Hz), 6.83 (1H, s), 4.16 (2H, t, J 7.4 Hz), 2.95 (2H, t, J 7.5 Hz), 1.46 (6H, s), MS (ESI) 451 (MH+).

EXAMPLE 11

Resin Bound 4-[4-(1-tertbutoxycarbonylamino-1-methylethyl)phenyl]-5-chloro-N-[4-(2-hydroxyethyl)phenyl]pyrimidine-2-amine (1)

A slurry of polystyrene sulphonyl chloride resin (Argonaut Technologies, 520 mg, 2.4 mmol/g, 1.24 mmol equivalent) in anhydrous dichloromethane (12 ml) was treated with 4-[4-(1-tertbutoxycarbonylamino-1-methylethyl) phenyl]-5-chloro-N-[4-(2-hydroxyethyl) phenyl]pyrimidine-2-amine (2.40 g, 4.97 mmol), N,N-diethylisopropylamine (0.64 g, 4.97 mmol) and anhydrous pyridine (4 mL) and the resulting mixture agitated at room temperature for 18 h. The resin was filtered and washed sequentially with dichloromethane, methanol, N,N-dimethylformamide and dichloromethane then air dried to give the sulphonate derivatised resin (1).

EXAMPLE 12

4-[4-(1-Amino-1-methylethyl)phenyl]-5-chloro-N-[4-(2-(2-methylimidazol-1-yl)ethyl)phenyl]pyrimidine-2-amine A mixture of derivatised resin (1) (55 mg), N,N-diethylisopropylamine (38 mg, 0.30 mmol), and 2-methylimidazole (8 mg, 0.10 mmol) in anhydrous acetonitrile (2 ml) was heated at 70° for 18 h, with agitation. The mixture was allowed to cool to room temperature then diluted with anhydrous tetrahydrofuran (2 ml) and treated with polystyrene methylisocyanate (Argonaut Technologies, 120 mg, 1.65 mmol/g, 0.2 mmol equivalent) and macroporous triethylammonium methylpolystyrene carbonate (Argonaut Technologies, 38 mg, 2.64 mmol/g, 0.1 mmol equivalent). The resulting mixture was agitated at room temperature for 6 h, then filtered and washed once with dichloromethane. The combined filtrate and washings were evaporated to dryness under a stream of nitrogen, then resuspended in dichloromethane (1 mL) and treated with trifluoroacetic acid (1 mL) for 1 h at room temperature. The mixture was evaporated to give the title compound (19.4 mg).

HPLC-MS Retention time 1.93 min; MH+ 447
HPLC-MS

HPLC-MS was performed on a Hewlett Packard 1100/MSD ES Single Quadropole system with diode array detector using a Luna C18(2) 50×2.0 mm (3 μm) column, running a gradient of 95% [0.1% aqueous formic acid], 5% [0.1% formic acid in acetonitrile] to 10% [0.1% aqueous formic acid], 90% [0.1% formic acid in acetonitrile] over 2 min, then maintaining the mobile phase at that ratio for a further 1 min. Flow rate 0.8 ml/min. MS was acquired by API electrospray in positive ion mode, at 70V, scanning from 150 to 750 amu.

The following compounds of examples 13 to 25 were prepared in a similar manner to the compound of example 12, each using the starting material shown in place of 2-methylimidazole:

EXAMPLE 13

4-[4-(1-Amino-1-methylethyl)phenyl]-5-chloro-N-[4-(2-(2-ethylimidazol-1-yl)ethyl)phenyl]pyrimidine-2-amine 2-Ethylimidazole gave the title compound (16.1 mg)
HPLC-MS Retention time 1.96 min; MH+ 461

EXAMPLE 14

4-[4-(1-Amino-1-methylethyl)phenyl]-5-chloro-N-[4-(2-(2-isopropylimidazol-1-yl)ethyl)phenyl]pyrimidine-2-amine 2-Isopropylimidazole gave the title compound (12.8 mg)
HPLC-MS Retention time 1.98 min; MH+ 475

EXAMPLE 15

4-[4-(1-Amino-1-methylethyl)phenyl]-5-chloro-N-[4-2-(4,5-dichloroimidazol-1-yl)ethyl)phenyl]pyrimidine-2-amine 4,5-Dichloroimidazole gave the title compound (20.4 mg)
HPLC-MS Retention time 2.27 min; MH+ 501

EXAMPLE 16

4-[4-(1-Amino-1-methylethyl)phenyl]-5-chloro-N-[4-(2-(benzimidazol-1-yl)ethyl)phenyl]pyrimidine-2-amine Benzimidazole gave the title compound (16.4 mg)
HPLC-MS Retention time 2.04 min; MH+ 483

EXAMPLE 17

4-[4-(1-Amino-1-methylethyl)phenyl]-5-chloro-N-[4-(2-(thiomorpholino)ethyl)phenyl]pyrimidine-2-amine Thiomorpholine gave the title compound (22.0 mg)
HPLC-MS Retention time 1.93 min; MH+ 468

EXAMPLE 18

4-[4-(1-Amino-1-methylethyl)phenyl]-5-chloro-N-[4-(2-(tertbutylamino)ethyl)phenyl]pyrimidine-2-amine tertButylamine gave the title compound (20.4 mg)
HPLC-MS Retention time 1.94 min; MH+ 438

EXAMPLE 19

4-[4-(1-Amino-1-methylethyl)phenyl]-5-chloro-N-[4-(2-(4-methylpiperazin-1-yl)ethyl)phenyl]pyrimidine-2-amine 1-Methylpiperazine gave the title compound (17.4 mg)
HPLC-MS Retention time 1.84 min; MH+ 465

EXAMPLE 20

4-[4-(1-Amino-1-methylethyl)phenyl]-5-chloro-N-[4-(2-(4-ethylpiperazin-1-yl)ethyl)phenyl]pyrimidine-2-amine 1-Ethylpiperazine gave the title compound (22.1 mg)
HPLC-MS Retention time 1.85 min; MH+ 479

EXAMPLE 21

4-[4-(1-Amino-1-methylethyl)phenyl]-5-chloro-N-[4-(2-(3,5-dimethylpiperazin-1-yl)ethyl)phenyl]pyrimidine-2-amine 2,6-Dimethylpiperazine gave the title compound (3.1 mg)
HPLC-MS Retention time 1.93 min; MH+ 479

EXAMPLE 22

4-[4-(1-Amino-1-methylethyl)phenyl]-5-chloro-N-[4-(2-(4-(pyrid-2-yl)piperazin-1-yl)ethyl)phenyl]pyrimidine-2-amine 4-(Pyrid-2-yl)piperazine gave the title compound (15.3 mg)
HPLC-MS Retention time 1.92 min; MH+ 528

EXAMPLE 23

4-[4-(1-Amino-1-methylethyl)phenyl]-5-chloro-N-[4-(2-(pyrrolidin-1-yl)ethyl)phenyl]pyrimidine-2-amine Pyrrolidine gave the title compound (5.6 mg)
HPLC-MS Retention time 1.93 min; MH+ 436

EXAMPLE 24

4-[4-(1-Amino-1-methylethyl)phenyl]-5-chloro-N-[4-(2-(piperidin-1-yl)ethyl)phenyl]pyrimidine-2-amine Piperidine gave the title compound (19.1 mg)
HPLC-MS Retention time 1.94 min; MH+ 450

EXAMPLE 25

(R)-4-[4-(1-Amino-1-methylethyl)phenyl]-5-chloro-N-[4-(2-(3-dimethylaminopyrrolidin-1-yl)ethyl)phenyl]pyrimidine-2-amine (R)-3-Dimethylaminopyrrolidine gave the title compound (23.1 mg)
HPLC-MS Retention time 1.75 min; MH+ 479

EXAMPLE 26

4-[4-(1-Amino-1-methylethyl)phenyl]-5-chloro-N-[4-(2-morphoinoethyl)phenyl]pyrimidine-2-amine maleic acid salt To a hot solution of the compound of Example 9 (50 mg, 0.11 mmol) in ethanol (2 ml) was added a solution of maleic acid (13 mg, 0.11 mol) in ethanol (1 ml) and the mxiture stirred at room temperature for 1 h. The solution was partially concentrated in vacuo and diethyl ether added to give the desired product as a white precipitate. The precipitate was collected by filtration and washed with diethyl ether to give the title compound as a white solid (49 mg). m.p. 179–182°. δH ($d^6$ DMSO) 9.85 (1H, s), 8.64 (1H, s), 8.32 (1H, bs), 7.94 (2H, d, J 8.5 Hz), 7.71 (2H, d, J 8.5 Hz), 7.64 (2H, d, J 8.5 Hz), 7.15 (2H, d, J 8.5 Hz), 6.02 (2H, s), 3.61 (4H, bs), 3.31 (3H, bs), 2.69–2.50 (8H, m), 1.69 (6H, s).

Biological Activity

The following assays were used to demonstrate the activity and selectivity of compounds according to the invention:

The activity of the comounds against KDR kinase and FGFR2 kinase can be determined in the following two assays:

KDR Kinase and FGFr2 Kinase

The activities of recombinant KDR kinase and FGFr2 kinase were determined by measuring their ability to transfer the γ-phosphate from [$^{33}$P]ATP to polyglutamic acid-tyrosine (pEY).

The assay methodology employed for both kinases is identical except that in the assay of KDR kinase the diluent used throughout was 20 mM HEPES pH 7.25 containing 2 mM $MnCl_2$, 2 mM $MnCl_2$, 5 mM DTT and 0.05% Brij 35, whereas in the FGFr2 assay 10 mM $MnCl_2$ is used instead of 2 mM $MnCl_2$ and 2 mM $MnCl_2$.

The assay was conducted in a total volume of 202 μl containing 1–10 ng kinase, 5 μg/ml pEY (4:1) (Sigma, UK), 1 μM ATP (containing~50,000 cpm [$^{33}$P]ATP (Amersham International, UK) (Sigma, UK) and test inhibitors at the appropriate concentration. The test inhibitors were dissolved in DMSO and added such that the final concentration of DMSO in the assay did not exceed 2% (v/v). The assay was initiated by addition of kinase and terminated after 10 minutes incubation at room temperature by addition of 50 μl of 20 mM HEPES pH 7.25 containing 0.125M EDTA and 10 mM ATP. A 200 μl aliquot was applied to the well of a Millipore (UK) MAFC filter plate containing 100 μl of 30% (w/v) trichloroacetic acid (TCA). The plate was then placed on a suitable manifold and connected to a vacuum. After complete elimination of the liquid each well was washed under vacuum using five volumes (100 μl per wash) of 10% (w/v) TCA and finally two volumes (100 μl per wash) of ethanol. The bottom of the filter plate was then sealed and 100 μl per well of Ultima Gold (Beckham, UK) scintillant was added to each well. The readioactivity was measured using an appropiate scintillation counter such as a Wallac Trilux or Packard TopCount. The $IC_{50}$ value for each inhibitor was obtained from log dose inhibition curves fitted to the four-parameters logistic equation.

In this assay the most active compounds accoding to the invention have $IC_{50}$ values of around 1 μM and below.

The selectivity of compounds according to the invention can be determined in the following assays:

p56$^{lck}$ Kinase Assay

The tyrosine kinase activity of p56$^{lck}$ was determined using a RR-src peptide (RRLIEDNEYTARG) and [γ-$^{33}$P]

ATP as substrates. Quantitation of the $^{33}$P-phosphorylated peptide formed by the action of p56$^{lck}$ was achieved using an adaption of the method of Geissler et al (J. Biol. Chem. (1990) 265, 22255–22261).

All assays were performed in 20 mM HEPES pH 7.5 containing 10 mM MgCl$_2$, 10 mM MnCl$_2$, 0.05% Brij, 1M ATP (0.5 μCi[γ-$^{33}$P]ATP) and 0.8 mg/ml RR-src. Inhibitors in dimethylsulphoxide (DMSO) were added such that the final concentration of DMSO did not exceed 1%, and enzyme such that the consumption of ATP was less than 10%. After incubation at 30° C. for 15 min, the reaction was terminated by the addition of one-third volume of stop reagent (0.25 mM EDTA and 33 mM ATP in dH$_2$O). A 15 μl aliquot was removed, spotted onto a P-30 filtermat (Wallac, Milton Keynes, UK), and washed sequentially with 1% acetic acid and de-ionised water to remove ATP. The bound $^{33}$P-RR-src was quantitated by scintillation counting of the filtermat in a Betaplate scintillation counter (Wallac, Milton Keynes, UK) after addition of Meltilex scintillant (Wallac, Milton Keynes, UK).

The dpm obtained, being directly proportional to the amount of $^{33}$P-RR-src produced by p56$^{lck}$, were used to determine the IC$_{50}$ for each compound. The IC$_{50}$ was defined as the concentration of compound required to reduce the production of $^{33}$P-RR-src by 50%.

In this test, compounds according to the invention have IC$_{50}$ values of 10 μM and above.

Zap-70 Kinase Assay

The tyrosine kinase activity of Zap-70 was determined using a capture assay based on that employed above for p56$^{lck}$. The RR-src peptide was replaced with polyGlu-Tyr (Sigma; Poole, UK) at a final concentration of 17 μg/ml. After addition of the stopped reaction to the filtermat, trichloroacetic acid 10% (w/v) was employed as the wash reagent instead of acetic acid and a final wash in absolute ethanol was also performed before scintillation counting. IC$_{50}$ values were determined as described above in the p56$^{lck}$ assay.

In this test the compounds of the invention have IC$_{50}$ values of around 10 μM and above.

EGFr Kinase Assay

The tyrosine kinase activity of the EGF receptor (EGFr) was determined using a similar methodology to the p56$^{lck}$ kinase assay, except that the RR-src peptide was replaced by a peptide substrate for EGFr obtained from Amersham International plc (Little Chalfont, UK) and used at the manufacturer's recommended concentration. IC$_{50}$ values were determined as described previously in the p56$^{lck}$ assay.

Protein Kinase C Assay

Inhibitor activity against protein kinase C (PKC) was determined using PKC obtained from Sigma Chemical Company (Poole, UK) and a commercially available assay system (Amersham International plc, Amersham, UK). Briefly, PKC catalyses the transfer of the γ-phosphate ($^{32}$p) of ATP to the threonine group on a peptide specific for PKC. Phosphorylated peptide is bound to phosphocellulose paper and subsequently quantified by scintillation counting. The inhibitor potency is expressed as either (i) the concentration required to inhibit 50% of the enzyme activity (IC$_{50}$) or (ii) the percentage inhibition achieved by 10 μM inhibitor.

In this test the compounds of the invention have IC$_{50}$ values of around 10 μM and above.

What is claimed is:
1. A compound of formula (1):

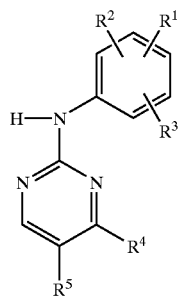

wherein
R$^1$ is a —XR$^6$ group;
X is a covalent bond, —O—, —S—, —C(O)—, —C(S)—, —C(O)O—, —S(O)—, S(O$_2$)—, —CH$_2$—, or —N(R$^7$)—;
R$^7$ is a hydrogen atom or a straight or branched alkyl group;
R$^6$ is a hydrogen or halogen atom or an optionally substituted aliphatic, cycloaliphatic, heteroaliphatic, heterocycloaliphatic, aromatic or heteroaromatic group, or a —NO$_2$, —CN, —SO$_2$N(R$^8$)(R$^9$), —CON(R$^8$)(R$^9$), —CSN(R$^8$)(R$^9$), —NH$_2$ or substituted amino group;
R$^8$ and R$^9$, which may be the same or different are a hydrogen atom or an optionally substituted aliphatic, cycloaliphatic, heteroaliphatic, heterocycloaliphatic, aromatic or heteroaromatic group;
R$^2$ and R$^3$ are each a hydrogen atom;
R$^4$ is a X$^1$R$^{11}$ group;
X$^1$ is a covalent bond or a —C(R$^{12}$)(R$^{13}$)— or —C(O)— group;
R$^{12}$ and R$^{13}$ are each a hydrogen or halogen atom or a hydroxyl, alkyl or haloalkyl group;
R$^{11}$ is an optionally substituted phenyl, thienyl, thiazolyl or indolyl group;
R$^5$ is a halogen atom or an alkynyl group;
and the salts, solvates, hydrates and N-oxides thereof.
2. A compound which is:
4-[4-(1-Amino-1-methylethyl)phenyl]-5-chloro-N-[4-(2-hydroxyethyl)phenyl]pyrimidine-2-amine;
4-[4-(1-Amino-1-methylethyl)phenyl]-5-chloro-N-[3-(2-hydroxyethyl)phenyl]pyrimidine-2-amine;
4-[4-(1-Amino-1-methylethyl)phenyl]-5-chloro-N-[4-(1-imidazolyl)phenyl]pyrimidine-2-amine;
4-[4-(1-Amino-1-methylethyl)-3-fluorophenyl]-5-chloro-N-[4-(2-hydroxyethyl)phenyl]pyrimidine-2-amine;
4-[4-(1-Amino-1-methylethyl)phenyl]-5-chloro-N-[4-(2-(imidazol-1-yl)ethyl)phenyl]pyrimidine-2-amine;
4-[4-(1-Amino-1-methylethyl)phenyl]-5-chloro-N-[4-(2-(2-methylimidazol-1-yl)ethyl)phenyl]pyrimidine-2-amine;
4-[4-(1-Amino-1-methylethyl)phenyl]-5-chloro-N-[4-(2-(2-isopropylimidazol-1-yl)ethyl)phenyl]pyrimidine-2-amine;
4-[4-(1-Amino-1-methylethyl)phenyl]-5-chloro-N-[4-(2-(4-thiomorpholino)ethyl)phenyl]pyrimidine-2-amine;
4-[4-(1-Amino-1-methylethyl)phenyl]-5-chloro-N-[4-(2-(tertbutylamino)ethyl)phenyl]pyrimidine-2-amine;
4-[4-(1-Amino-1-methylethyl)phenyl]-5-chloro-N-[4-(2-(4-methylpiperazin-1-yl)ethyl)phenyl]pyrimidine-2-amine;
4-[4-(1-Amino-1-methylethyl)phenyl]-5-chloro-N-[4-(2-(4-ethylpiperazin-1-yl)ethyl)phenyl]pyrimidine-2-amine;

4-[4-(1-Amino-1-methylethyl)phenyl]-5-chloro-N-[4-(2-(3,5-dimethylpiperazin-1-yl)ethyl)phenyl]pyrimidine-2-amine;

4-[4-(1-Amino-1-methylethyl)phenyl]-5-chloro-N-[4-(2-(4-(pyrid-2-yl)piperazin-1-yl)ethyl)phenyl]pyrimidine-2-amine;

4-[4-(1-Amino-1-methylethyl)phenyl]-5-chloro-N-[4-(2-(pyrrolidin-1-yl)ethyl)phenyl]pyrimidine-2-amine;

4-[4-(1-Amino-1-methylethyl)phenyl]-5-chloro-N-[4-(2-(piperidin-1-yl)ethyl)phenyl]pyrimidine-2-amine;

(R)-4-[4-(1-Amino-1-methylethyl)phenyl]-5-chloro-N-[4-(2-(3-dimethylaminopyrrolidin-1-yl)ethyl)phenyl]pyrimidine-2-amine;

and the salts, solvates, hydrates and N-oxides thereof.

* * * * *